US010559381B2

(12) United States Patent
Kuji et al.

(10) Patent No.: US 10,559,381 B2
(45) Date of Patent: Feb. 11, 2020

(54) MEDICAL SYSTEM AND INFORMATION NOTIFICATION METHOD

(71) Applicant: OLYMPUS CORPORATION, Tokyo (JP)

(72) Inventors: Tetsuya Kuji, Tokyo (JP); Katsuyoshi Ishibashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 852 days.

(21) Appl. No.: 15/081,508

(22) Filed: Mar. 25, 2016

(65) Prior Publication Data
US 2016/0210419 A1 Jul. 21, 2016

Related U.S. Application Data

(63) Continuation of application No. PCT/JP2015/059490, filed on Mar. 26, 2015.

(30) Foreign Application Priority Data

Apr. 10, 2014 (JP) ................................ 2014-081462

(51) Int. Cl.
*G16H 40/20* (2018.01)
*G16H 40/40* (2018.01)
(Continued)

(52) U.S. Cl.
CPC ............. *G16H 40/20* (2018.01); *G06Q 10/06* (2013.01); *G06Q 50/28* (2013.01); *G16H 40/40* (2018.01);
(Continued)

(58) Field of Classification Search
CPC ........ G06Q 10/06; G06Q 50/28; G16H 40/20; G16H 40/40
See application file for complete search history.

(56) References Cited

U.S. PATENT DOCUMENTS 6,820,157 B1 * 11/2004 Eide ....................... G06F 8/656
710/303
2002/0126204 A1 9/2002 Takeshige et al.
(Continued)

FOREIGN PATENT DOCUMENTS

JP 2002-092183 A 3/2002
JP 2002-263063 A 9/2002
(Continued)

OTHER PUBLICATIONS

Jun. 23, 2015 Search Report issued in International Patent Application No. PCT/JP2015/059490.
(Continued)

*Primary Examiner* — Neal Sereboff
(74) *Attorney, Agent, or Firm* — Oliff PLC

(57) ABSTRACT

A server device includes a first storage unit in which first information including device names, locations, and scheduled use dates and times of a plurality of medical devices is stored, a determination unit that determines an alternative medical device that may be an alternative device of the failed medical device on the basis of second information relating to at least one failure of the plurality of medical devices and the first information stored in the first storage unit, and a communication unit that transmits third information including a device name, a location, and a usable date and time of the alternative medical device to one or more client terminal devices corresponding to the medical devices that have not failed.

6 Claims, 35 Drawing Sheets

(51) Int. Cl.
  *G06Q 50/28* (2012.01)
  *G06Q 10/06* (2012.01)
  *A61B 18/14* (2006.01)
  *A61B 1/00* (2006.01)

(52) U.S. Cl.
  CPC ....... *A61B 1/00059* (2013.01); *A61B 18/1402* (2013.01); *A61B 2018/1412* (2013.01)

(56) References Cited

U.S. PATENT DOCUMENTS

| | | | | |
|---|---|---|---|---|
| 2003/0093503 A1* | 5/2003 | Yamaki | ................... | G06F 19/00 709/220 |
| 2004/0030610 A1* | 2/2004 | Mimura | ............... | G06Q 10/087 705/305 |
| 2006/0252991 A1* | 11/2006 | Kubach | ............. | A61B 1/00057 600/118 |
| 2007/0005202 A1* | 1/2007 | Breed | ............... | B60W 50/0205 701/29.1 |
| 2007/0094535 A1* | 4/2007 | Prasee | ..................... | B25J 5/007 714/5.11 |
| 2009/0192519 A1* | 7/2009 | Omori | .................... | A61B 34/30 606/130 |
| 2009/0204232 A1* | 8/2009 | Guru | ....................... | G06Q 10/06 700/9 |
| 2012/0271645 A1* | 10/2012 | Dain | ...................... | G06Q 10/00 705/1.1 |
| 2013/0317694 A1* | 11/2013 | Merg | .................... | G07C 5/008 701/31.6 |
| 2014/0249838 A1* | 9/2014 | Gelb | ...................... | G16H 50/50 705/2 |

FOREIGN PATENT DOCUMENTS

| | | |
|---|---|---|
| JP | 2005-043996 A | 2/2005 |
| JP | 2013-228946 A | 11/2013 |

OTHER PUBLICATIONS

Jun. 23, 2015 Written Opinion issued in International Patent Application No. PCT/JP2015/059490.

Dec. 1, 2015 Decision to Grant of Japanese Patent Application No. 2015-543981.

* cited by examiner

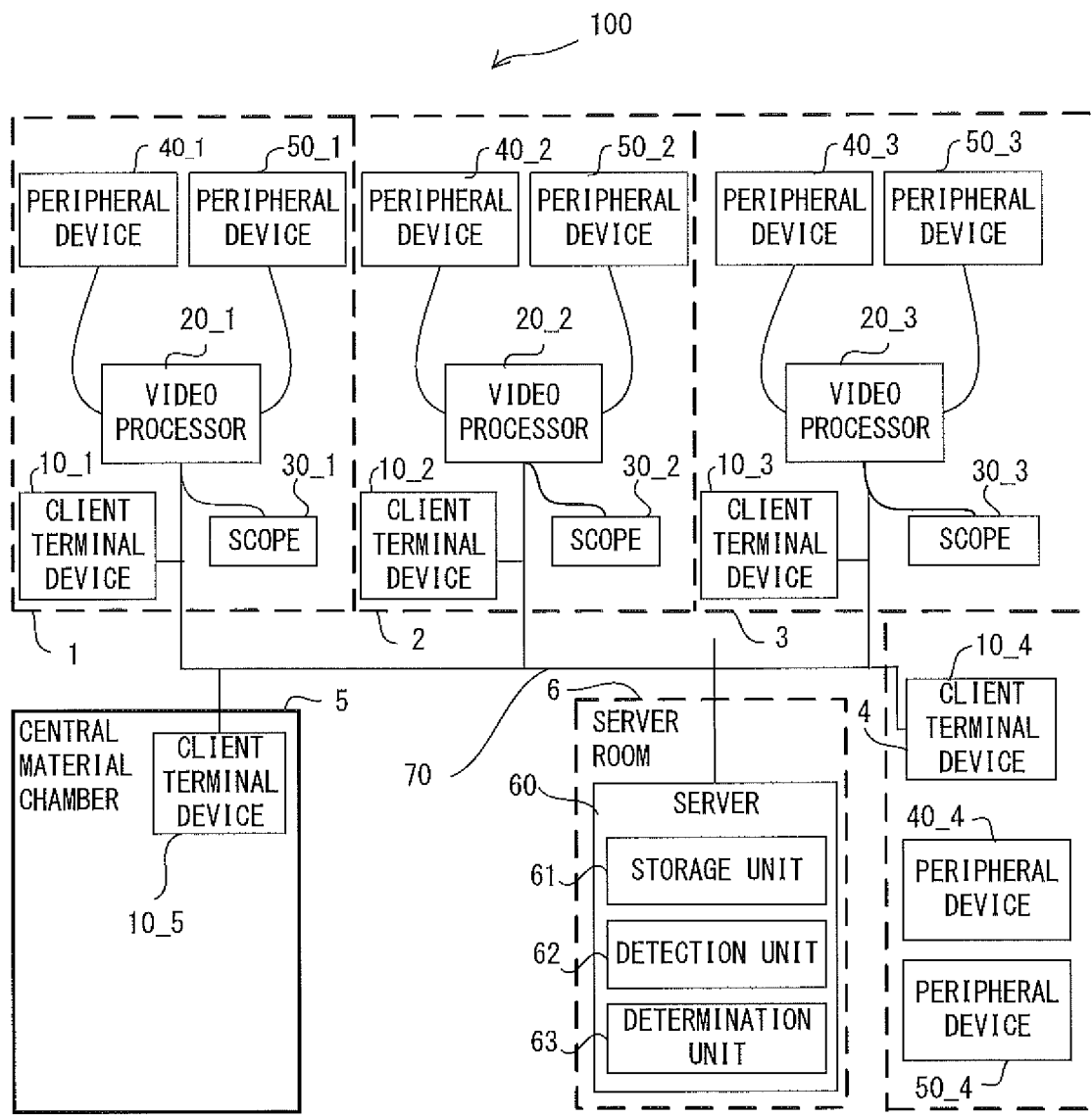
F I G. 1

| DEVICE NAME | SERIAL NO. | POWER SUPPLY /CONNECTION | LOCATION | SCHEDULED USE |
|---|---|---|---|---|
| VIDEO PROCESSOR 20_1 | AAAAAAAA | ON | INSPECTION ROOM 1 | 11:00~11:20 |
| VIDEO PROCESSOR 20_1 | AAAAAAAA | | INSPECTION ROOM 1 | 11:30~11:50 |
| VIDEO PROCESSOR 20_1 | AAAAAAAA | | INSPECTION ROOM 1 | ⋮ |
| VIDEO PROCESSOR 20_2 | BBBBBBBB | | INSPECTION ROOM 2 | 16:45~17:00 |
| VIDEO PROCESSOR 20_3 | CCCCCCCC | ON | INSPECTION ROOM 3 | 11:05~11:25 |
| VIDEO PROCESSOR 20_3 | CCCCCCCC | | INSPECTION ROOM 3 | 11:35~11:55 |
| VIDEO PROCESSOR 20_3 | CCCCCCCC | | INSPECTION ROOM 3 | ⋮ |
| PERIPHERAL DEVICE 40_4 | DDDDDDDD | | STOREHOUSE | NONE |
| ⋮ | ⋮ | ⋮ | ⋮ | ⋮ |

FIG. 2

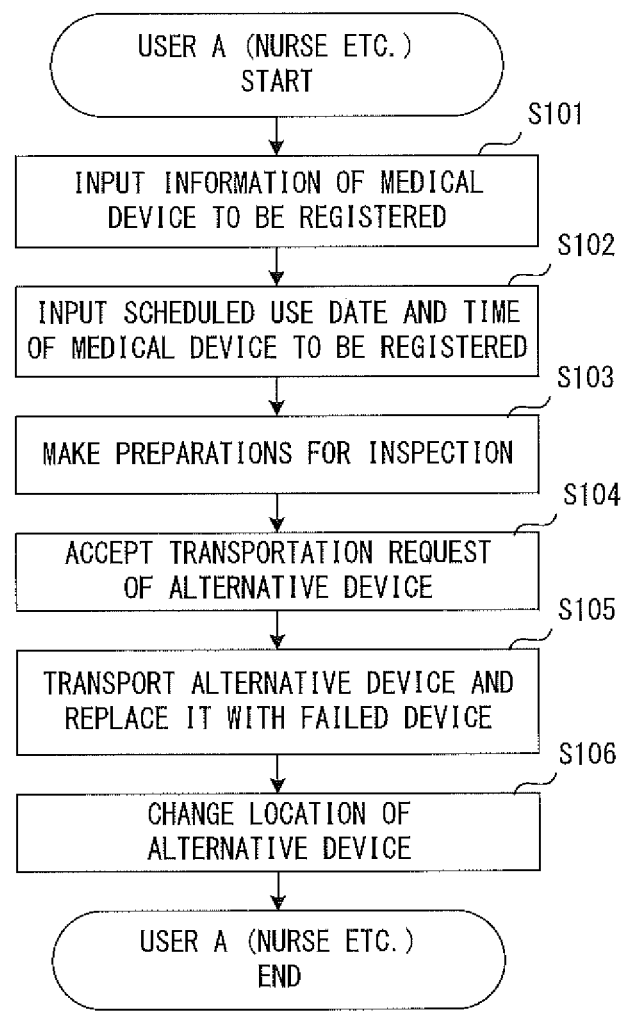
F I G. 3

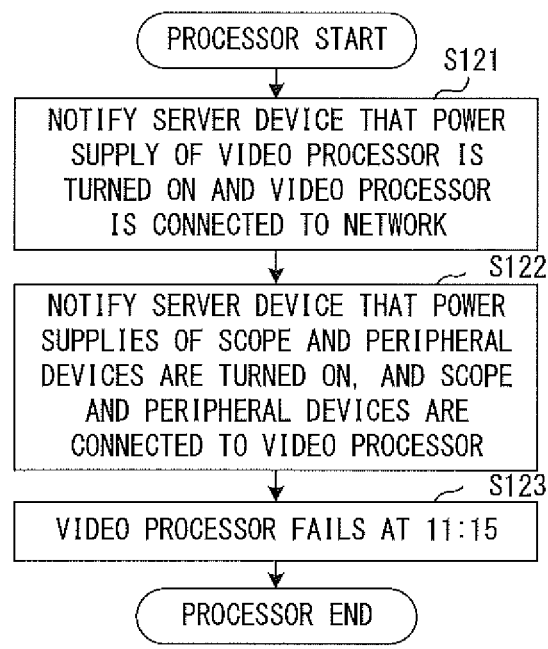
F I G. 5

DEVICE REGISTRATION

DEVICE NAME          SERIAL NO.

101    102
LOCATION  103   104  REGISTRATION
STOREHOUSE ▼    105  CANCEL

F I G. 8

SCHEDULED DEVICE USE DATE
AND TIME INPUT

113 — DEVICE NAME | SERIAL NO. | LOCATION
VIDEO PROCESSOR 20_1 ▼ | AAAAAAAA | INSPECTION ROOM 1

111 — SCHEDULED USE START ~ SCHEDULED USE END

112 — CONFIRMATION

CANCEL

114

F I G. 9

DEVICE FAILURE INFORMATION

A video processor 20_1
has failed in
an inspection room 1.   /121

CLOSE

FIG. 10

ALTERNATIVE DEVICE INFORMATION

| | DEVICE NAME | SERIAL NO. | LOCATION | USABLE DATE AND TIME |
|---|---|---|---|---|
| ● | VIDEO PROCESSOR 20_2 | BBBBBBBB | INSPECTION ROOM 2 | ~16:45 |
| ○ | VIDEO PROCESSOR 20_3 | CCCCCCCC | INSPECTION ROOM 3 | — |

131

132 — INSPECTION CONTINUATION

INSPECTION END — 133

F I G. 1 1

DEVICE TRANSPORTATION REQUEST

ACCEPT.
Move the following device to the inspection room 1.

| DEVICE NAME | SERIAL NO. | LOCATION |
|---|---|---|
| VIDEO PROCESSOR 20_2 | BBBBBBBB | INSPECTION ROOM 2 |

152

CLOSE

F I G. 1 4

LOCATION CHANGE OF DEVICE

| DEVICE NAME | SERIAL NO. | LOCATION |
|---|---|---|
| VIDEO PROCESSOR 20_2 ▼ | BBBBBBBB | INSPECTION ROOM 2 |

161 ─ (pointing to DEVICE NAME field)

PRESENT LOCATION    162    LOCATION AFTER CHANGE
INSPECTION ROOM 2    INSPECTION ROOM 1 ▼

163 ─ CONFIRMATION    CANCEL ─ 164

F I G. 1 5

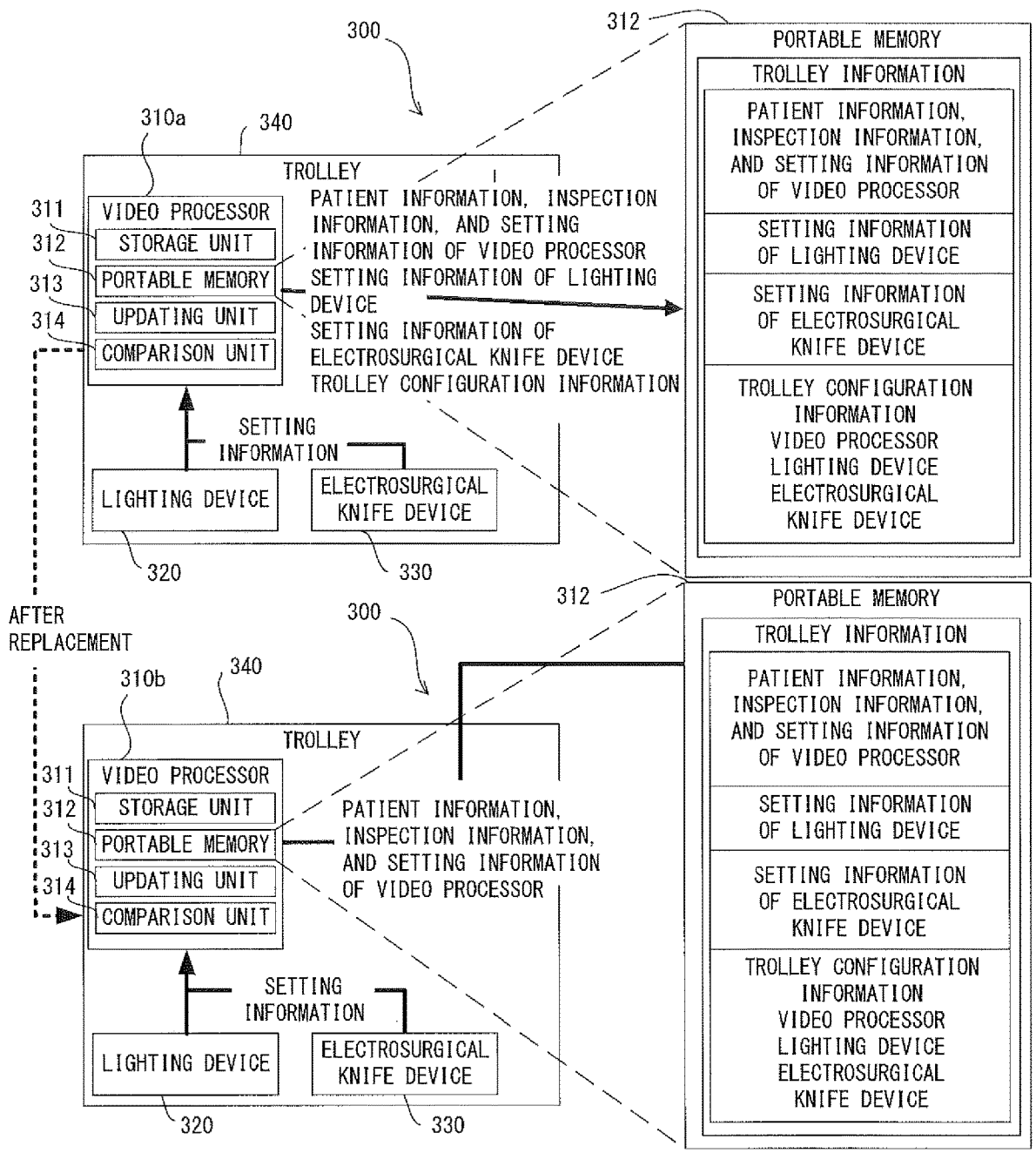
F I G. 2 3

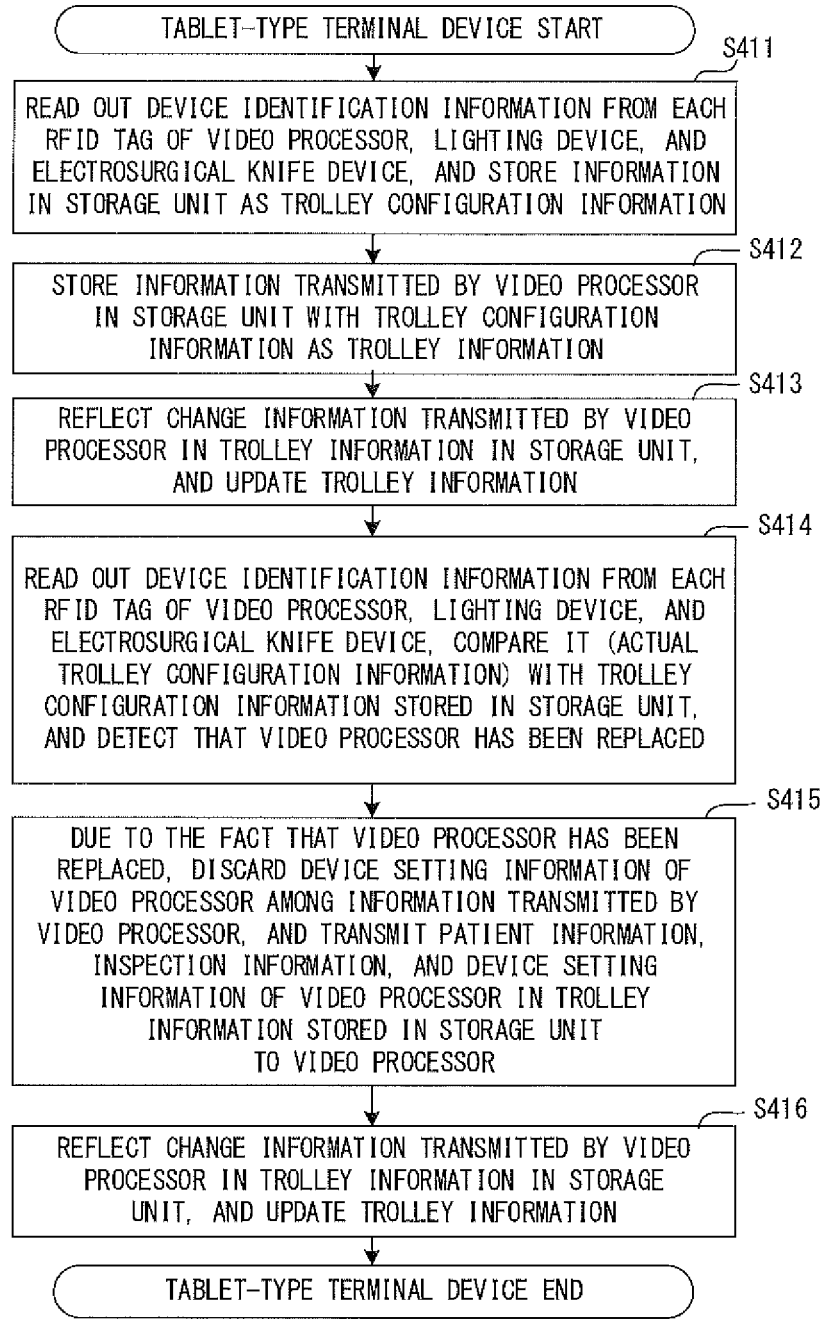
F I G. 3 1

MEDICAL SYSTEM AND INFORMATION NOTIFICATION METHOD

CROSS-REFERENCE TO RELATED APPLICATIONS

This application is based upon and claims the benefit of priority of the prior Japanese Patent Application No. 2014-081462, filed Apr. 10, 2014, the entire contents of which are incorporated herein by reference.

This is a Continuation Application of PCT Application No. PCT/JP2015/059490, filed Mar. 26, 2015, which was not published under PCT Article 21 (2) in English.

FIELD

The embodiments discussed herein are related to a server device, a medical system, and an information notification method used in a medical institution or the like.

BACKGROUND

Conventionally, as a medical system used in a medical institution or the like, for example, an endoscope system used in a hospital is included. An endoscope system has, for example, a configuration that includes an endoscope processor to which a scope (an endoscope), a monitor, and the like are connected, and in which the endoscope processor is connected to an in-hospital LAN (Local Area Network). In addition, an endoscope processor and a scope, a monitor, and the like that are connected to the endoscope processor are generally provided in the same room (e.g., an inspection room).

In the above-described endoscope system, when a device (e.g., a scope) that is connected to the endoscope processor fails, this fact is displayed on the monitor and reported to a user (e.g., a doctor or a nurse). That is, the fact is reported to a user that is in the same room. In such a case, the user that has confirmed the notification makes contact with persons concerned (a maintenance person, etc.), confirms the presence or absence, location, and the like of an alternative device, and replaces the failed device with the alternative device.

In the medical system, in addition to the above-described endoscope system, various other types of systems are known. For example, a medical device management system (see Japanese Laid-open Patent Publication No. 2002-92183 etc.) that manages medical devices in a medical site, an endoscope system (see Japanese Laid-open Patent Publication No. 2002-263063 etc.) including an endoscope processor that processes image signals from an electronic endoscope and displays images on a monitor, a medical service support system (see Japanese Laid-open Patent Publication No. 2013-228946 etc.) that manages statuses of medical devices used in a medical service, and the like are known.

SUMMARY

According to a first aspect of the present invention, a server device is provided including a first storage unit in which first information including device names, locations, and scheduled use dates and times of a plurality of medical devices are stored, a determination unit that determines an alternative medical device that may be an alternative device of the failed medical device on the basis of second information relating to at least one failure of the plurality of medical devices and the first information stored in the first storage unit, and a communication unit that transmits third information including a device name, a location, and a usable date and time of the alternative medical device to one or more client terminal devices corresponding to the medical devices that have not failed.

According to a second aspect of the present invention, in the first aspect, the server device in the first aspect is provided, wherein the plurality of medical devices include an endoscopic device and one or more peripheral devices connected to the endoscopic device, and the second information is transmitted from the endoscopic device that has detected a failure of the peripheral device.

According to a third aspect of the present invention, a medical system is provided including the server device in the second aspect and the plurality of medical devices including the endoscopic device and the peripheral device, wherein the endoscopic device includes a second storage unit in which patient information and inspection information are stored, a third storage unit in which the patient information and the inspection information stored in the second storage unit, device identification information and device setting information of the endoscopic device, and device identification information and device setting information of the peripheral device acquired from the peripheral device are associated with each other and stored, and that is freely attached to or detached from the endoscopic device, an updating unit that updates corresponding information stored in the third storage unit in response to a change in the patient information or the inspection information stored in the second storage unit, a change in device setting of the endoscopic device, or the device setting information after a change in the peripheral device acquired from the peripheral device, and a comparison unit that compares the device identification information of the endoscopic device and the device identification information of the peripheral device acquired from the peripheral device with the device identification information of the endoscopic device and the device identification information of the peripheral device stored in the third storage unit, as a result of a comparison performed by the comparison unit, when the device identification information of the endoscopic device is different, the endoscopic device stores the patient information and the inspection information stored in the third storage unit in the second storage unit of the endoscopic device, and performs device setting of the endoscopic device in accordance with the device setting information of the endoscopic device stored in the third storage unit, and as result of a comparison performed by the comparison unit, when the device identification information of the peripheral device is different, the endoscopic device performs device setting of the peripheral device in accordance with the device setting information of the peripheral device stored in the third storage unit.

According to a fourth aspect of the present invention, a medical system is provided including the server device in the second aspect, the plurality of medical devices including the endoscopic device and the peripheral device, and a portable terminal device, wherein the endoscopic device includes a second storage unit in which patient information and inspection information are stored, the endoscopic device transmits one or more of the patient information stored in the second storage unit, the inspection information stored in the second storage unit, device setting information of the endoscopic device, and device setting information of the peripheral device acquired from the peripheral device to the portable terminal device, the portable terminal device includes an acquisition unit that acquires one or both of device identification information of the endoscopic device and device identification information of the peripheral device, a third storage unit in which the patient information and the inspection information stored in the second storage unit, the device identification information and the device setting information of the endoscopic device, and the device identification information and the device setting information of the peripheral device are associated with each other and stored, an updating unit that updates corresponding information stored in the third storage unit in response to the patient information, the inspection information, the device setting information of the endoscopic device, or the device setting information of the peripheral device after a change transmitted by the endoscopic device, and a comparison unit that compares the device identification information of the endoscopic device and the device identification information of the peripheral device acquired by the acquisition unit with the device identification information of the endoscopic device and the device identification information of the peripheral device stored in the third storage unit, as a result of a comparison performed by the comparison unit, when the device identification information of the endoscopic device is different, the portable terminal device transmits the patient information, the inspection information, and the device setting information of the endoscopic device stored in the third storage unit to the endoscopic device, the endoscopic device stores the patient information and the inspection information transmitted by the portable terminal device in the second storage unit of the endoscopic device, and performs device setting of the endoscopic device in accordance with the device setting information of the endoscopic device transmitted by the portable terminal device, and as a result of a comparison performed by the comparison unit, when the device identification information of the peripheral device is different, the portable terminal device transmits the device setting information of the peripheral device stored in the third storage unit to the endoscopic device, and the endoscopic device performs device setting of the peripheral device in accordance with the device setting information of the peripheral device transmitted by the portable terminal device.

According to a fifth aspect of the present invention, an information notification method is provided for a medical system including a plurality of medical devices, one or more client terminal devices, and a server device including a storage unit that stores first information including device names, locations, and scheduled use dates and times of the plurality of medical devices, wherein the server device determines an alternative medical device that may be an alternative device of the medical device that has failed, on the basis of second information including a device name and a location of the medical device that has failed and is at least one of the plurality of medical devices and the first information stored in the storage unit, and transmits third information including a device name, a location, and a usable date and time of the alternative medical device to the one or more client terminal devices corresponding to the medical devices that have not failed.

BRIEF DESCRIPTION OF DRAWINGS

FIG. 1 illustrates a configuration example of a medical system according to a first embodiment.
FIG. 2 illustrates a data structure example of information stored in a storage unit.
FIG. 3 illustrates an operation example of a user A (e.g., a nurse).
FIG. 5 illustrates an operation example of a video processor.
FIG. 8 is a first display screen example displayed on a display unit of the server device.
FIG. 9 is a second display screen example displayed on the display unit of the server device.
FIG. 10 is a first display screen example displayed on a display unit of the client terminal device.
FIG. 11 is a second display screen example displayed on the display unit of the client terminal device.
FIG. 14 is a fifth display screen example displayed on the display unit of the client terminal device.
FIG. 15 is a sixth display screen example displayed on the display unit of the client terminal device.
FIG. 23 illustrates a configuration example of a medical system according to a third embodiment.
FIG. 31 illustrates an operation example of a tablet-type terminal device.

DESCRIPTION OF EMBODIMENTS

Figure 4:
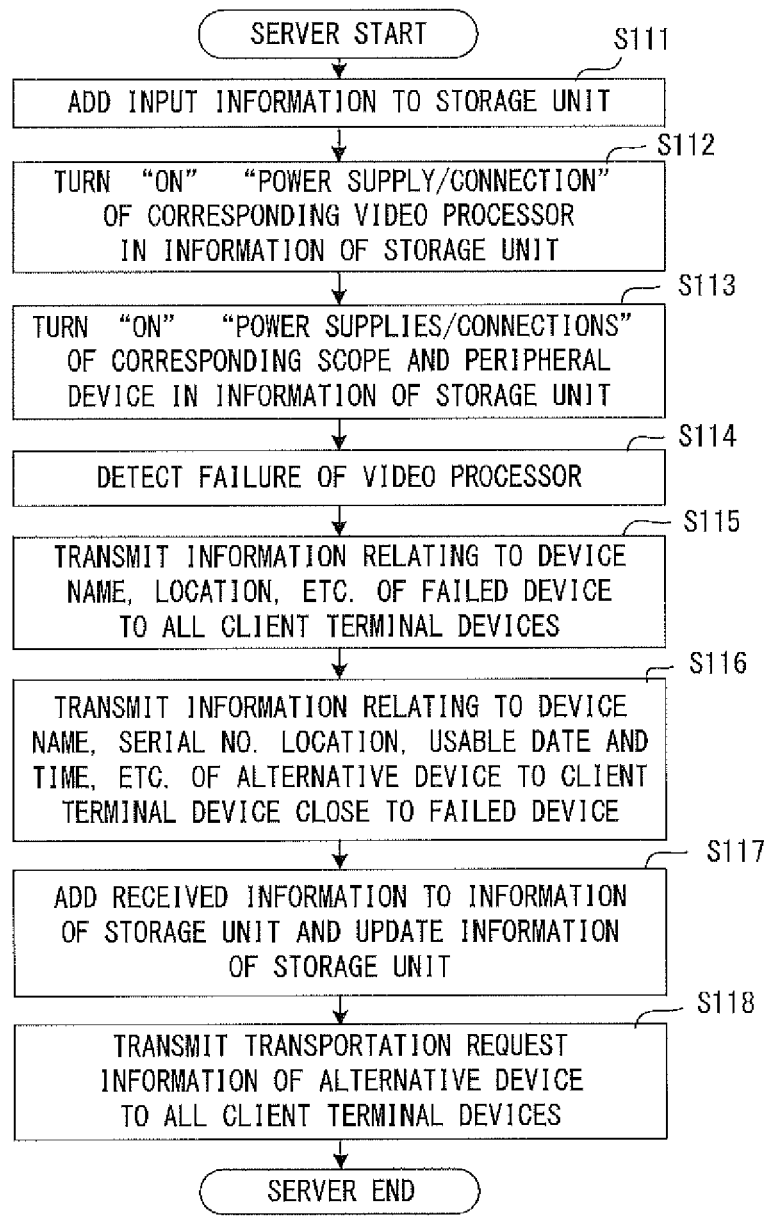
FIG. 4 illustrates an operation example of a server device.

Hereinafter, embodiments of the present invention will be described with reference to the accompanying drawings.

First Embodiment

FIG. 1 illustrates a configuration example of a medical system according to a first embodiment of the present invention.

As illustrated in FIG. 1, the medical system 100 according to the present embodiment is provided on a medical institution (e.g., a hospital) including inspection rooms 1, 2, and 3, a storehouse 4, a central material chamber 5, and a server room 6.

In each of the inspection rooms 1, 2, and 3, a client terminal device 10 (10_1, 10_2, or 10_3), a video processor 20 (20_1, 20-2, or 20_3), and the like are provided, and a scope 30 (30_1, 30_2, or 30_3), a peripheral device 40 (40_1, 40_2, or 40_3), a peripheral device 50 (50_1, 50_2, or 50_3), and the like are connected to the video processor 20.

In the storehouse 4, a client terminal device 10_4, a peripheral device 40_4, a peripheral device 50_4, and the like are provided. The peripheral device 40_4 and the peripheral device 50_4 are peripheral devices provided as spares.

In the central material chamber 5, a client terminal device 10_5 and the like are provided.

In the server room 6, a server device 60 and the like are provided.

Further, the client terminal device 10, the video processor 20, and the server device 60 are connected to a network 70 including one or both of wire and radio in an in-hospital LAN etc. and can transmit and receive information to and from each other.

As described above, the medical system 100 according to the present embodiment has a configuration that includes a plurality of the client terminal devices 10 (10_1, 10_2, 10_3, 10_4, and 10_5), a plurality of the video processors 20 (20_1, 20_2, and 20_3), a plurality of the scopes 30 (30_1, 30_2, and 30_3), a plurality of the peripheral devices 40 (40_1, 40_2, 40_3, and 40_4), a plurality of the peripheral devices 50 (50_1, 50_2, 50_3, and 50_4), and the server device 60, and in which each client terminal device 10, each video processor 20, and the server device 60 are connected to the network 70.

In the medical system 100 having such a configuration, the peripheral devices 40 and 50 are, for example, a lighting device and an electrosurgical knife device. Further, the scope 30 is also an electronic endoscope, and is an example of a peripheral device different from the peripheral devices 40 and 50. Further, the video processor 20 is also an endoscope processor, and is an example of an endoscopic device. Further, the plurality of the video processors 20, the plurality of the scopes 30, the plurality of the peripheral devices 40, and the plurality of the peripheral devices 50 are an example of a plurality of medical devices. Further, the plurality of the client terminal devices 10 are an example of one or more client terminal devices. Further, the video processor 20 includes a monitor (not illustrated). Further, each of the client terminal device 10 and the server device 60 includes an input unit and a display unit (not illustrated).

In the medical system 100 having such a configuration, the video processor 20 processes a video signal output from the scope 30 and displays an image on the monitor, or detects a failure of the peripheral devices and transmits information relating to a failed peripheral device to the server device 60 in the connected peripheral devices (the scope 30 and the peripheral devices 40 and 50). In addition, the video processor 20 detects a failure of the peripheral device, for example, depending on the presence or absence of a response from the peripheral device.

The server device 60 includes a storage unit 61, a detection unit 62, and a determination unit 63, and performs detection of a failure of the medical device, determination of an alternative medical device that may be an alternative device of the failed medical device, or the like.

In the storage unit 61, as described later in detail with reference to FIG. 2, information relating to device names, serial Nos, power supplies/connections, locations, scheduled uses, and the like of the plurality of medical devices is stored.

The detection unit 62 detects the failure of the medical device. For example, the detection unit 62 detects a failure of the video processor 20 depending on the presence or absence of a response from the video processor 20. Further, for example, the detection unit 62 detects a failure of the peripheral devices (the scope 30 and the peripheral devices 40 and 50) connected to the video processor 20 on the basis of information relating to the failed peripheral device transmitted by the video processor 20.

On the basis of information stored in the storage unit 61, the determination unit 63 determines an alternative medical device that may be an alternative device of the failed medical device.

Further, the server device 60 transmits information relating to a device name, a location, and the like of the failed medical device to one or more client terminal devices 10, and also transmits information relating to a device name, a location, a usable date and time, and the like of the alternative medical device to one or more client terminal devices 10. In this case, for example, the server device 60 may transmit information relating to the device name, the location, and the like of the failed medical device to all the client terminal devices 10, and also may transmit the information relating to the device name, the location, the usable date and time, and the like of the alternative medical device to the client terminal device 10 close to the failed medical device.

The client terminal device 10 displays on the display unit the information relating to the device name, the location, and the like of the failed medical device transmitted by the server device 60, or the information relating to the device name, the location, the usable date and time, and the like of the alternative medical device.

FIG. 2 illustrates a data structure example of information stored in the storage unit 61.

As illustrated in FIG. 2, the information stored in the storage unit 61 includes information relating to "device names", "serial Nos", "power supplies/connections", "locations", and "scheduled uses" of the plurality of medical devices. The "serial No" is a number uniquely attached to the medical device, and is an example of device identification information. The "power supply/connection" is information to be described as "ON" only when a present time is a date and time included in the "scheduled use", and a power supply of the medical device is turned ON and the medical device is directly or indirectly connected to the network 70 (the server device 60). The "location" is information indicating a location of the medical device. The "scheduled use" is information indicating a date and time at which use is scheduled. Note that information in which only a time is indicated, as in for example "11:00 to 11:20" illustrated in FIG. 2, indicates that a date at which use is scheduled is the same day as the present date, and "none" illustrated in FIG. 2 indicates that use is not scheduled.

Next, an operation example (including an information notification operation as well) of the medical system 100 according to the present embodiment will be described.

To facilitate understanding of the above, in this explanation, an operation example of a user as well as operation examples of the client terminal device 10, the video processor 20, and the server device 60 will be described.

Figure 6:
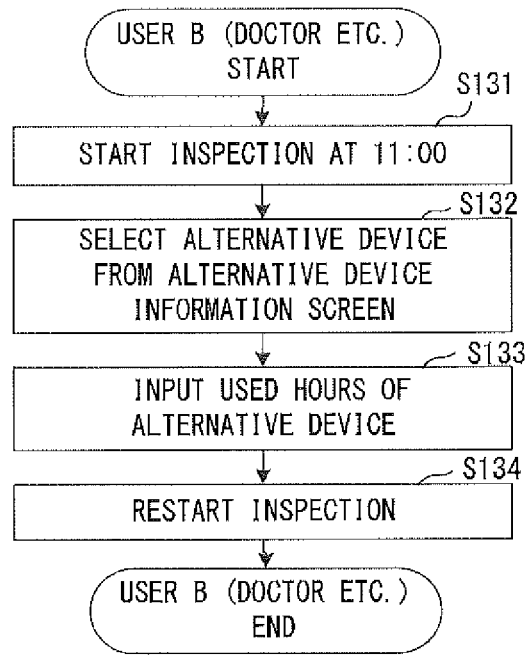
FIG. 6 illustrates an operation example of a user B (e.g., a doctor).
Figure 7:
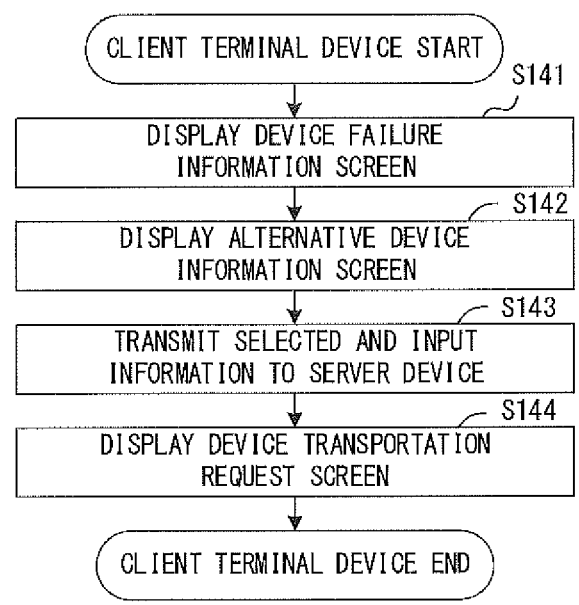
FIG. 7 illustrates an operation example of a client terminal device.

FIG. 3 illustrates an operation example of a user A (e.g., a nurse). FIG. 4 illustrates an operation example of the server device 60. FIG. 5 illustrates an operation example of the video processor 20. FIG. 6 illustrates an operation example of a user B (e.g., a doctor). FIG. 7 illustrates an operation example of the client terminal device 10. FIGS. 8 and 9 are display screen examples displayed on the display unit of the server device 60. FIGS. 10 to 15 are display screen examples displayed on the display unit of the client terminal device 10.

In this operation example, as illustrated in FIG. 3, the user A first operates the input unit of the server device 60, displays a device registration screen illustrated in FIG. 8 on the display unit of the server device 60, and inputs information of a medical device to be registered (S101 of FIG. 3). In more detail, the user A operates the input unit of the server device 60, and inputs a device name and a serial No of the medical device to be registered to input boxes 101 and 102 of the device registration screen illustrated in FIG. 8. Further, the user A selects a location from a pull-down box 103 and depresses a registration button 104. On this device registration screen, the user A operates the input unit of the server device 60 and depresses a cancel button 105, thereby canceling information input of the medical device to be registered.

After S101 of FIG. 3, an input screen of a scheduled device use date and time illustrated in FIG. 9 is displayed on the display unit of the server device 60, and subsequently, the user A operates the input unit of the server device 60 and inputs a scheduled use date and time of the medical device to be registered (S102 of FIG. 3). In more detail, the user A operates the input unit of the server device 60, inputs the scheduled use date and time (a scheduled use start and a scheduled use end) of the medical device to be registered in a scheduled use date and time input box 111 of an input screen of the scheduled device use date and time illustrated in FIG. 9, and depresses a confirmation button 112. In addition, on the scheduled device use date and time input screen, the user A can input a plurality of scheduled use dates and times. Further, the user A operates the input unit of the server device 60 and selects the medical device registered in the past from the pull-down box 113, thereby adding or changing the scheduled use date and time of the medical device. Further, the user A operates the input unit of the server device 60 and depresses a cancel button 114, thereby canceling an input of the scheduled use date and time of the medical device to be registered.

After S101 and S102 of FIG. 3, as illustrated in FIG. 4, the server device 60 stores (adds) information relating to the medical device input in S101 and S102 of FIG. 3 in (to) the storage unit 61 (S111 of FIG. 4). Thereby, assume in this operation example that information relating to the video processor 20_1 illustrated in FIG. 2 is added (note that "ON" of "power supply/connection" is excluded).

After S111 of FIG. 4, as illustrated in FIG. 3, the user A makes preparations to perform an inspection (S103 of FIG. 3). Assume in this operation example that the user A makes preparations to perform an inspection in an inspection room 1. Thereby, assume in this operation example that each device is connected to each other device as illustrated in the inspection room 1 of FIG. 1, and a power supply of each device of the video processor 20_1, the scope 30_1, and the peripheral devices 40_1 and 50_1 is turned ON.

After S103 of FIG. 3, as illustrated in FIG. 5, the video processor 20_1 notifies the server device 60 that a power supply of the video processor 20_1 is turned ON and the video processor 20_1 is connected to the network 70 (S121 of FIG. 5).

After S121 of FIG. 5, as illustrated in FIG. 4, the server device 60 that has received the notification turns "ON", as illustrated in FIG. 2, "power supply/connection" of the corresponding video processor 20_1 in the information stored in the storage unit 61 (S112 of FIG. 4).

After S112 of FIG. 4, as illustrated in FIG. 5, the video processor 20_1 detects that power supplies of the scope 30_1 and the peripheral devices 40_1 and 50_1 are turned ON and the scope 30_1 and the peripheral devices 40_1 and 50_1 are connected to the video processor 20_1, and notifies the server device 60 of this fact (S122 of FIG. 5).

After S122 of FIG. 5, as illustrated in FIG. 4, the server device 60 that has received the notification turns "ON" "power supplies/connections" of the corresponding scope 30_1 and peripheral devices 40_1 and 50_1 in the information stored in the storage unit 61 (S113 of FIG. 4).

After S113 of FIG. 4, as illustrated in FIG. 6, the user B starts an inspection in the inspection room 1 at 11:00 (S131 of FIG. 6).

Assume in this operation example that after S131 of FIG. 6, as illustrated in FIG. 5, the video processor 20_1 fails at 11:15 (S123 of FIG. 5).

After S123 of FIG. 5, as illustrated in FIG. 4, due to the fact that there is no response from the video processor 20_1, the server device 60 detects that the video processor 20_1 has failed (S114 of FIG. 4).

Subsequently, on the basis of the information stored in the storage unit 61, the server device 60 extracts information relating to the device name, the location, and the like of the failed video processor 20_1, and transmits the information to all the client terminal devices 10 (S115 of FIG. 4).

After S115 of FIG. 4, as illustrated in FIG. 7, each client terminal device 10 that has received the information displays a device failure information screen illustrated in FIG. 10 on the display unit on the basis of the information (S141 of FIG. 7). Thereby, the failure of the video processor 20_1 in the inspection room 1 is reported not only to the inspection room 1, but also to the other rooms on which the client terminal devices 10 are provided. Accordingly, even a user A that does not stay in the inspection room 1 can confirm the failure of the video processor 20_1 in the inspection room 1. On the device failure information screen illustrated in FIG. 10, for example, the user A operates the input unit of the client terminal device 10 and depresses a closing button 121, thereby closing the screen.

After S141 of FIG. 7, as illustrated in FIG. 4, on the basis of the information (see FIG. 2) stored in the storage unit 61, the server device 60 determines an alternative medical device that may be an alternative device of the failed video processor 20_1. Further, the server device 60 transmits the information relating to the device name, the serial No, the location, the usable date and time, and the like of the alternative medical device to the client terminal device 10_1 (the client terminal device 10_1 close to the failed video processor 20_1) in the inspection room 1 on which the failed video processor 20_1 is provided (S116 of FIG. 4). Assume in this operation example that on the basis of the fact that the failed medical device is the video processor 20_1, the video processors 20_2 and 20_3 are determined as an alternative medical device that may be the alternative device.

After S116 of FIG. 4, as illustrated in FIG. 7, on the basis of the information, the client terminal device 10_1 that has received the information displays an alternative device information screen illustrated in FIG. 11 on the display unit (S142 or FIG. 7). On this alternative device information screen, the device name, the serial No, the location, the usable date and time, and the like are displayed for each alternative medical device. Note that, with respect to the usable date and time, when a date is the same day as the present date, only a time indicated (see, for example, "to 16:45" of the "usable date and time" illustrated in FIG. 11). When a device is unusable (there is no usable date and time), "-" is indicated. Further, information relating to the unusable alternative medical device (e.g., the video processor 20_3) is displayed to be distinguished from the others (e.g., gray).

After S142 of FIG. 7, as illustrated in FIG. 6, the user B selects a desired alternative medical device in the alternative device information screen illustrated in FIG. 11 and displayed on the display unit of the client terminal device 10_1 (S132 of FIG. 6). In more detail, the user B operates the input unit of the client terminal device 10_1, depresses a radio button 131 corresponding to the desired alternative medical device from among alternative medical devices displayed on the alternative device information screen illustrated in FIG. 11, and depresses an inspection continuation button 132. Note that, in this alternative device information screen, it is impossible to select an unusable alternative medical device (e.g., the video processor 20_3). Assume in this operation example that the user B selects the video processor 20_2 here. In addition, in this alternative device information screen, the user B operates the input unit of the client terminal device 10_1 and depresses an inspection end button 133, thereby terminating an inspection.

Figure 12:
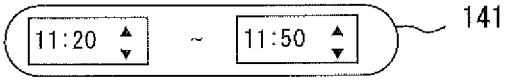
FIG. 12 is a third display screen example displayed on the display unit of the client terminal device.

After S132 of FIG. 6, the alternative device information screen illustrated in FIG. 12 is displayed on the display unit of the client terminal device 10_1. Subsequently, the user B operates the input unit of the client terminal device 10_1 and inputs used hours of the selected alternative medical device (S133 of FIG. 6). In more detail, the user B operates the input unit of the client terminal device 10_1, inputs a use start time and a use end time of the video processor 20_2 to a used hours input box 141 on the alternative device information screen illustrated in FIG. 12, and depresses a confirmation button 142. Assume, in this operation example, that the user B inputs "11:20" and "11:50" as the use start time and the use end time. In addition, in this alternative device information screen, the user B operates the input unit of the client terminal device 10_1 and depresses a cancel button 143, thereby returning to the last screen.

After S133 of FIG. 6, as illustrated in FIG. 7, the client terminal device 10_1 transmits information selected in S132 and input in S133 of FIG. 6 to the server device 60 (S143 of FIG. 7).

After S143 of FIG. 7, as illustrated in FIG. 4, the server device 60 that has received the information adds the information to information stored in the storage unit 61, and updates the information stored in the storage unit 61 (S117 of FIG. 4).

Subsequently, the server device 60 transmits information for requesting transportation of the alternative medical device (the video processor 20_2) selected in S132 of FIG. 6 to all the client terminal devices 10 (S118 of FIG. 4).

Figure 13:
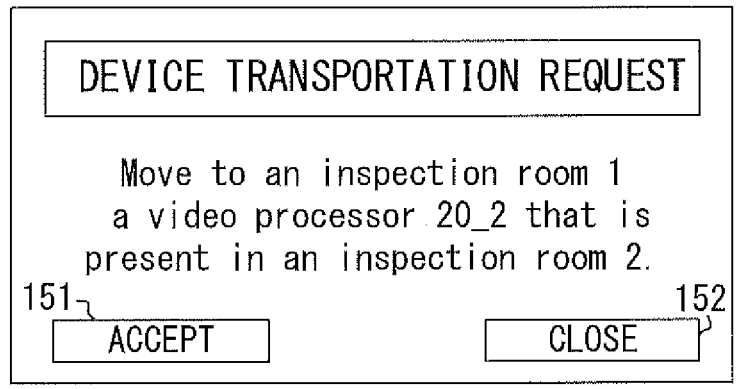
FIG. 13 is a fourth display screen example displayed on the display unit of the client terminal device.

After S118 of FIG. 4, as illustrated in FIG. 7, on the basis of the information, each client terminal device 10 that has received the information displays a device transportation request screen illustrated in FIG. 13 on the display unit (S144 of FIG. 7). Thereby, a transportation request of the alternative medical device is reported not only to the inspection room 1, but also to the other rooms in which the client terminal devices 10 are provided. Accordingly, even a user A that does not stay in the inspection room 1 can confirm the transportation request of the alternative medical device.

After S144 of FIG. 7, as illustrated in FIG. 3, a user A that has confirmed the transportation request of the alternative medical device accepts the transportation request (S104 of FIG. 3). In more detail, the user A depresses an acceptance button 151 on the device transportation request screen illustrated in FIG. 13 and displayed on the display unit of the client terminal device 10 (e.g., the client terminal devices 10 other than the client terminal device 10_1). When the user A accepts the device transportation request in this way, acceptance results thereof are subsequently displayed on the device transportation request screen, as illustrated in FIG. 14. On the device transportation request screen illustrated in FIGS. 13 and 14, the user A operates the input unit of the client terminal device 10 and depresses a closing button 152, thereby closing the screen.

Subsequently, the user A transports the alternative medical device (the video processor 20_2) in an inspection room 2 to the inspection room 1 and replaces it with the failed video processor 20_1 (S105 of FIG. 3).

After S105 of FIG. 3, a device location change screen illustrated in FIG. 15 is displayed on the display unit of the client terminal device 10_1. Subsequently, the user A operates the input unit of the client terminal device 10_1 and changes a location of the alternative medical device (the video processor 20_2) (S106 of FIG. 3). In more detail, the user A operates the input unit of the client terminal device 10_1, selects the alternative medical device and the location after the change from among pull-down boxes 161 and 162 on the device location change screen illustrated in FIG. 15, and depresses a confirmation button 163. In this operation example, the location of the video processor 20_2 is changed from the inspection room 2 to the inspection room 1. In addition, on this device location change screen, the user A operates the input unit of the client terminal device 10_1 and depresses a cancel button 164, thereby canceling the change in the location of the alternative medical device.

Further, when the change in the location is performed as described above, information relating to the change is transmitted from the client terminal device 10_1 to the server device 60, and the information stored in the storage unit 61 is updated on the basis of the information.

After S106 of FIG. 3, as illustrated in FIG. 6, the user B restarts an inspection in the inspection room 1 (S134 of FIG. 6).

As described above, when S106 of FIG. 3, S118 of FIG. 4, S123 of FIG. 5, S134 of FIG. 6, and S144 of FIG. 7 end, the operation example of the medical system 100 according to the present embodiment is completed.

In this operation example, an example of the case in which the video processor 20 has failed is described. When the scope 30 or the peripheral device 40 (or 50) has failed, although it is not described in detail, the failure is detected by the video processor 20 and this fact is reported to the server device 60, for example, in S123 of FIG. 5. Further, in S114 of FIG. 4, on the basis of the notification, a failure of the scope 30 or the peripheral device 40 is detected by the server device 60, and subsequent operations are performed in the same manner as in the operations at the time in which the failure of the video processor 20 has been detected.

As described above, according to the medical system 100 of the present embodiment, when the medical device (e.g., the video processor 20_1) fails, the information relating to the device name, the location, and the like of the failed medical device is reported to all the client terminal devices 10. Accordingly, not only a user that is in the same room as that of the failed medical device, but even a user that is in a room different from that of the failed medical device can confirm the notification.

Further, the information relating to the device name, the serial No, the location, the usable date and time, and the like of the alternative medical device that may be the alternative device of the failed medical device is reported to the client terminal device 10 close to the failed medical device. Accordingly, the user does not make contact with persons concerned and performs confirmation as in the conventional case, and only confirms information reported to the client terminal device 10 to thereby easily confirm the presence or absence, the location, and the like of the alternative medical device, and a burden on the user is reduced.

In the medical system 100 according to the present embodiment, various kinds of deformation are possible.

In the operation example of the medical system 100 according to the present embodiment, in S101 and S102 of FIG. 3, for example, the medical system 100 may be configured so as to perform, by the client terminal device 10, an input of the device registration and the scheduled use date and time of the medical device.

Further, in the operation example of the medical system 100 according to the present embodiment, in S116 of FIG. 4, for example, in the case of determining the alternative medical device that may be the alternative device of the failed video processor 20_1, for example, an unusable medical device maybe previously excluded from in-use medical devices. Further, on the alternative device information screen (see FIG. 11) displayed in S142 of FIG. 7, only usable medical devices may be displayed so as to be selected.

Second Embodiment

Figure 16:
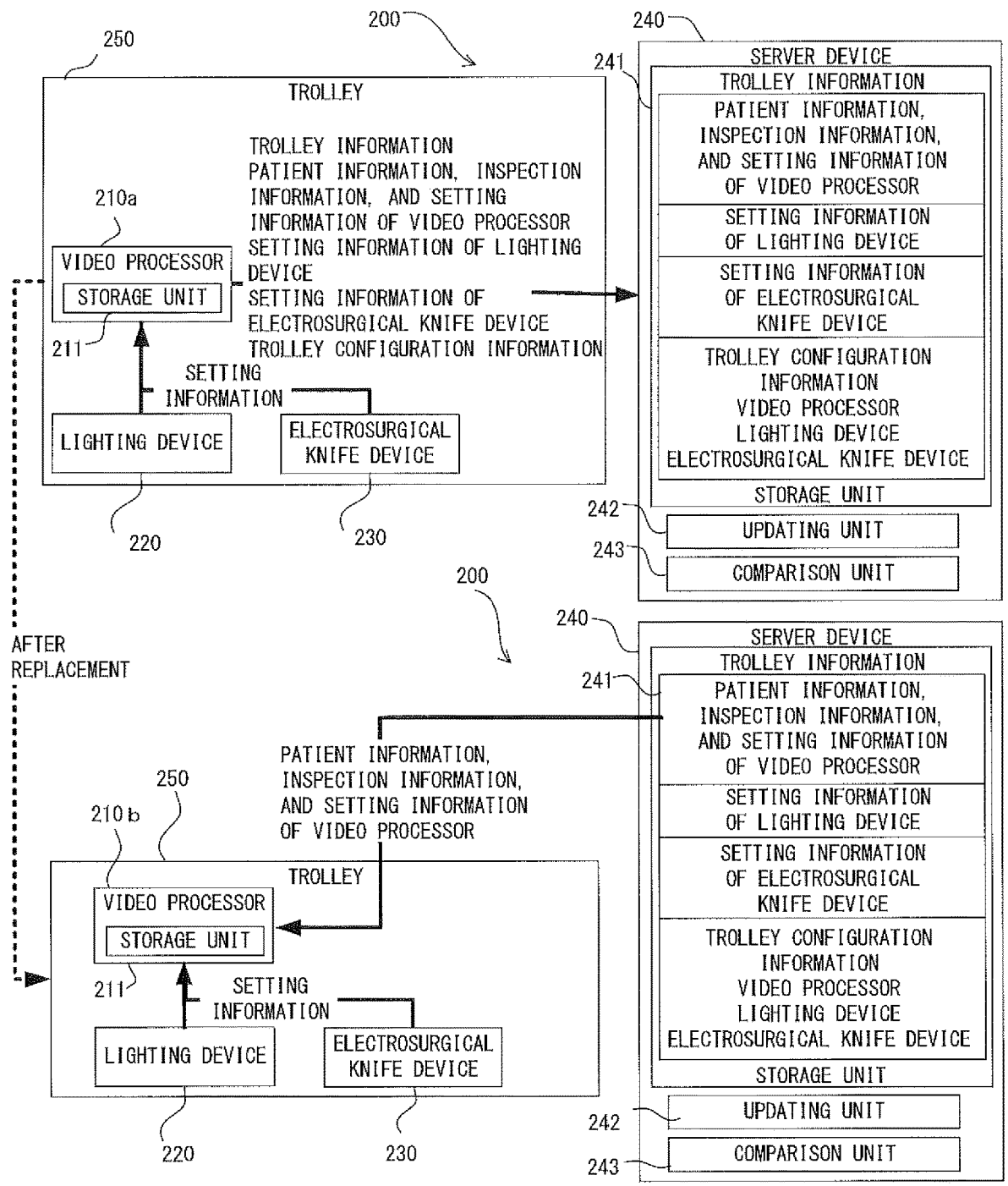
FIG. 16 illustrates a configuration example of a medical system according to a second embodiment.

FIG. 16 illustrates a configuration example of a medical system according to a second embodiment of the present invention.

In FIG. 16, an upper side illustrates a configuration including a video processor before a replacement and a lower side illustrates a configuration including a video processor after the replacement.

As illustrated at the upper side and the lower side of FIG. 16, the medical system 200 according to the present embodiment has a configuration that includes a video processor 210 (a video processor 210a before the replacement or a video processor 210b after the replacement), a lighting device 220, an electrosurgical knife device 230, and a server device 240, and in which the lighting device 220 and the electrosurgical knife device 230 are connected to the video processor 210, and the video processor 210 is connected to the server device 240 via a network (not illustrated). Further, the video processor 210, the lighting device 220, and the electrosurgical knife device 230 are mounted on a trolley 250.

The medical system 200 according to the present embodiment is, for example, a part of the medical system 100 according to the first embodiment. In this case, for example, the video processor 210 corresponds to the video processor 20, the lighting device 220 corresponds to the peripheral device 40, the electrosurgical knife device 230 corresponds to the peripheral device 50, and the server device 240 corresponds to the server device 60.

In the medical system 200 according to the present embodiment, the video processor 210 includes a storage unit 211.

In the storage unit 211, patient information relating to a patient, inspection information relating to an inspection, and the like are stored.

Further, the video processor 210 transmits to the server device 240 one or more of the patient information stored in the storage unit 211, the inspection information stored in the storage unit 211, device identification information of the video processor 210, device setting information of the video processor 210, device identification information of the peripheral devices (the lighting device 220 and the electrosurgical knife device 230) connected to the video processor 210, and device setting information of the peripheral devices (the lighting device 220 and the electrosurgical knife device 230) connected to the video processor 210. One or both of the device identification information and the device setting information of the lighting device 220 are acquired from the lighting device 220 by the video processor 210. Further, one or both of the device identification information and the device setting information of the electrosurgical knife device 230 are acquired from the electrosurgical knife device 230 by the video processor 210.

The server device 240 includes a storage unit 241, an updating unit 242, and a comparison unit 243.

In the storage unit 241, the patient information and the inspection information stored in the storage unit 211 of the video processor 210, the device identification information and the device setting information of the video processor 210, the device identification information and the device setting information of the peripheral devices (the lighting device 220 and the electrosurgical knife device 230) connected to the video processor 210, and the like are stored by being associated with each other as trolley information. Hereinafter, the device identification information of the devices (the video processor 210, the lighting device 220, and the electrosurgical knife device 230) mounted on the trolley 250 is also referred to as trolley configuration information.

The updating unit 242 updates corresponding information stored in the storage unit 241 in response to the patient information, the inspection information, the device setting information of the video processor 210, or the device setting information of the peripheral device (the lighting device 220 or the electrosurgical knife device 230), after the change, transmitted by the video processor 210.

The comparison unit 243 compares the device identification information of the video processor 210 and the device identification information of the peripheral devices (the lighting device 220 and the electrosurgical knife device 230) transmitted by the video processor 210 with the device identification information of the video processor 210 and the device identification information of the peripheral devices (the lighting device 220 and the electrosurgical knife device 230) stored in the storage unit 241.

In the medical system 200 according to the present embodiment, as described below in detail with reference to FIGS. 17 to 22, as a result of the comparison by the comparison unit 243, when the device identification information of the video processor 210 is different, it is recognized that the video processor 210 has been replaced. Further, the server device 240 transmits to the video processor 210 (210b) the patient information, the inspection information, and the device setting information of the video processor 210 (210a) stored in the storage unit 241. Further, the video processor 210 (210b) stores the patient information and the inspection information transmitted by the server device 240 in the storage unit 211 of the video processor 210 (210b). At the same time, the video processor 210 (210b) performs device setting of the video processor 210 (210b) in accordance with the device setting information of the video processor 210 (210a) transmitted by the server device 240.

Although it is not described in detail, as a result of the comparison by the comparison unit 243, when the device identification information of the peripheral device (the lighting device 220 or the electrosurgical knife device 230) is different, it is recognized that the peripheral device has been replaced. Further, the server device 240 transmits to the video processor 210 the device setting information of the peripheral device (the peripheral device before the replacement) stored in the storage unit 241. Further, the video processor 210 performs device setting of the peripheral device (the peripheral device after the replacement) in accordance with the device setting information of the peripheral device (the peripheral device before the replacement) transmitted by the server device 240.

Next, an operation example of the medical system 200 according to the present embodiment will be described.

Herein, an example of the case in which the replacement of the video processor 210 is performed due to a failure of the video processor 210 will be described as the operation example.

To facilitate understanding of the above, in this explanation, an operation example of a user (e.g., a doctor or a nurse) as well as operation examples of the video processor 210*a* before the replacement, the video processor 210*b* after the replacement, the lighting device 220, the electrosurgical knife device 230, and the server device 240 will be described.

Figure 17:
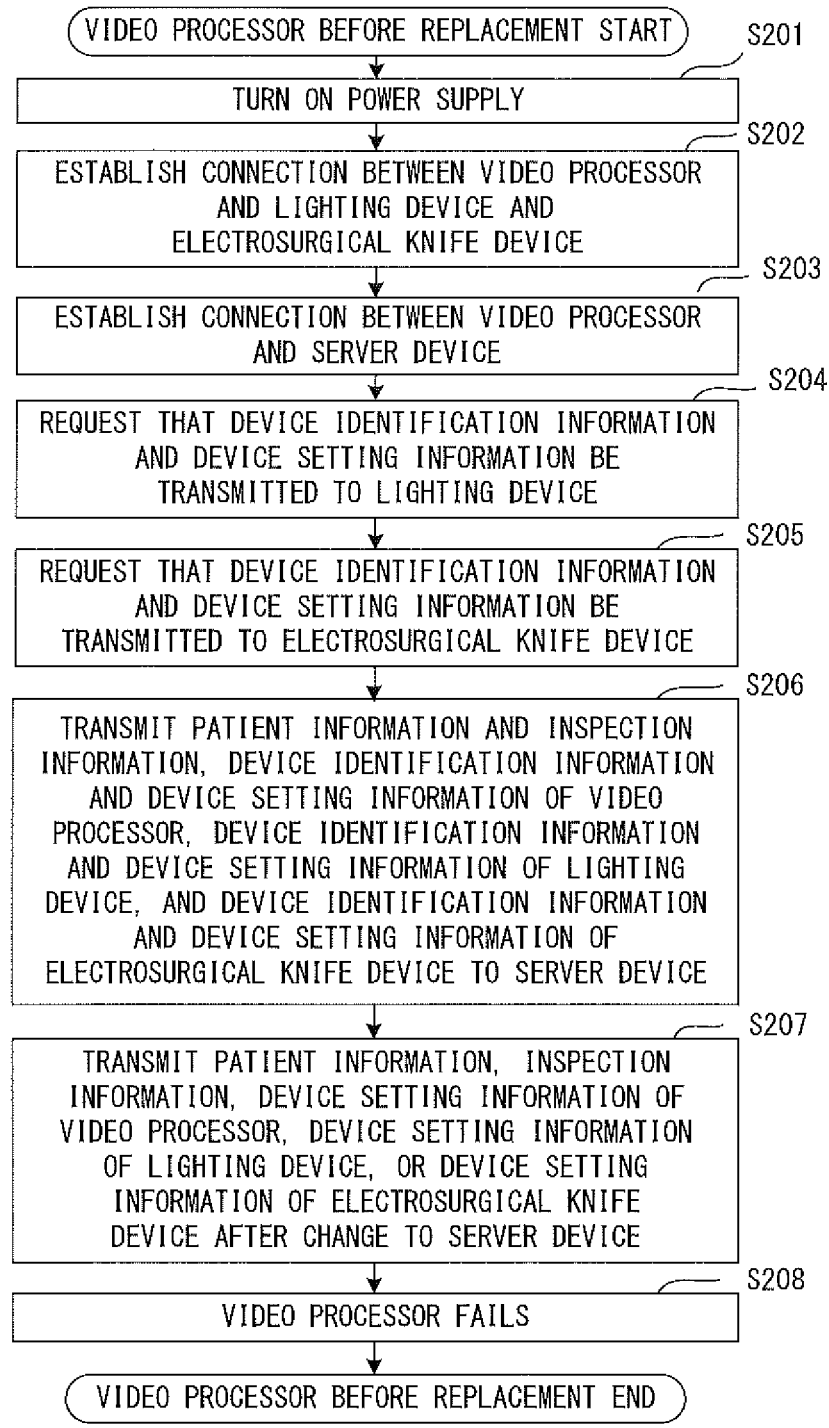
FIG. 17 illustrates an operation example of a video processor before a replacement.
Figure 18:
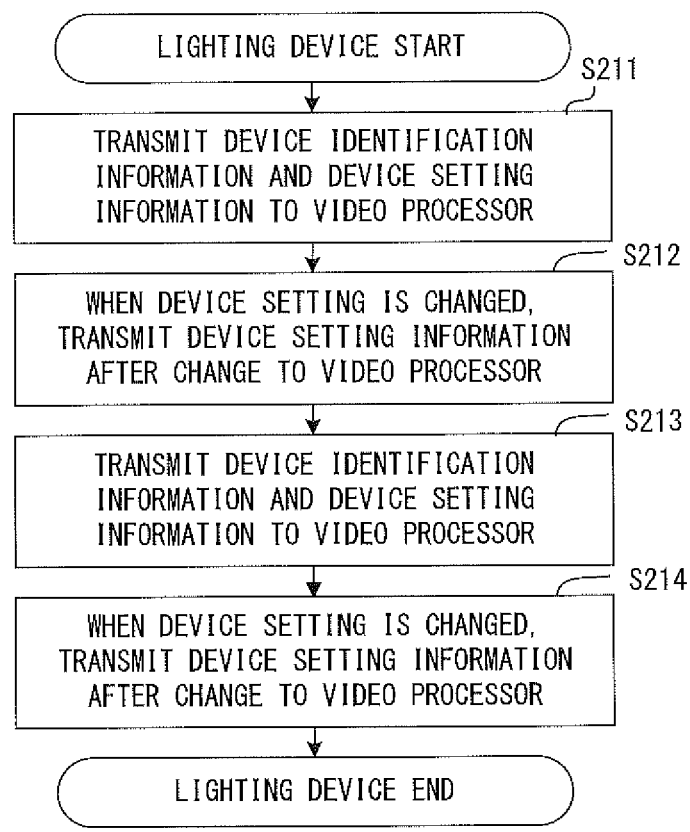
FIG. 18 illustrates an operation example of a lighting device.
Figure 19:
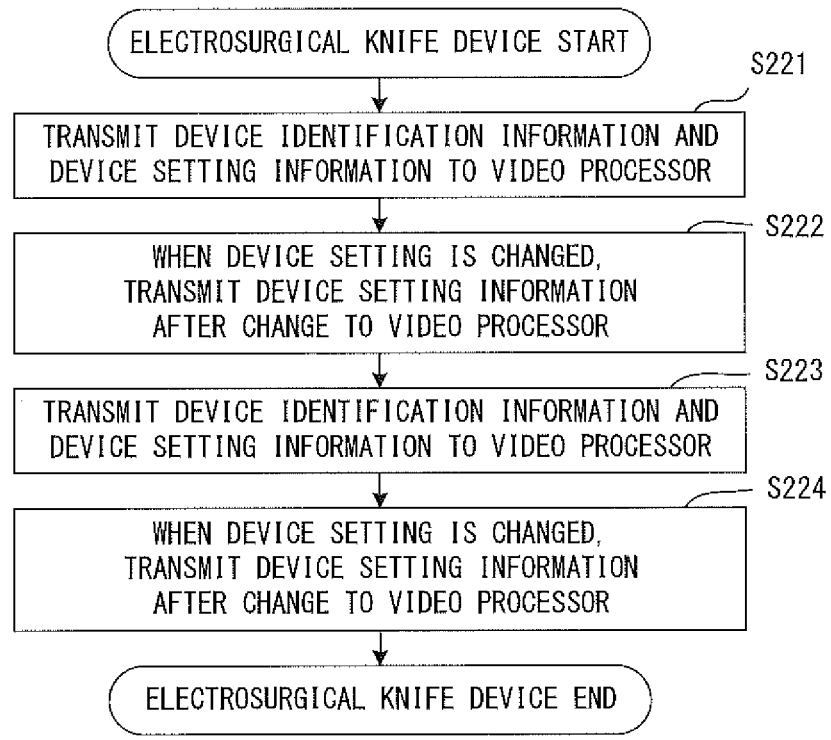
FIG. 19 illustrates an operation example of an electrosurgical knife device.
Figure 20:
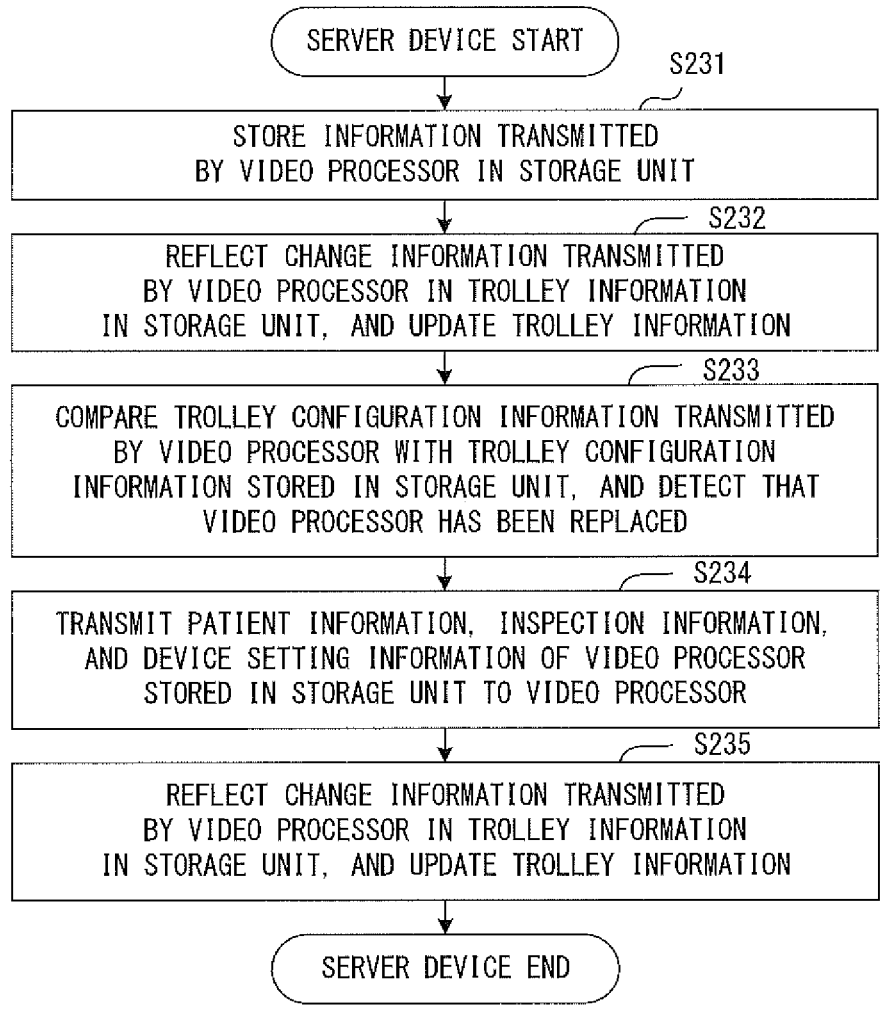
FIG. 20 illustrates an operation example of a server device.
Figure 21:
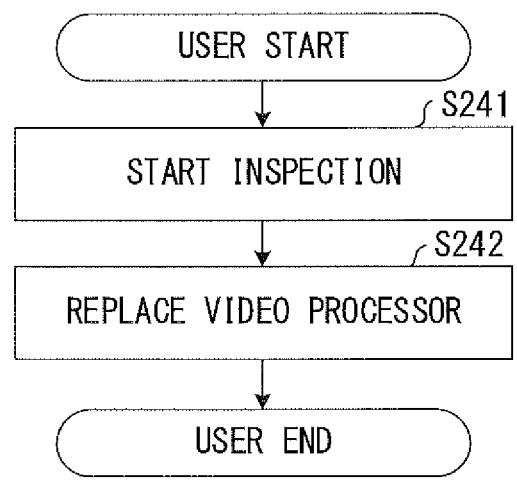
FIG. 21 illustrates an operation example of a user (e.g., a doctor or a nurse).
Figure 22:
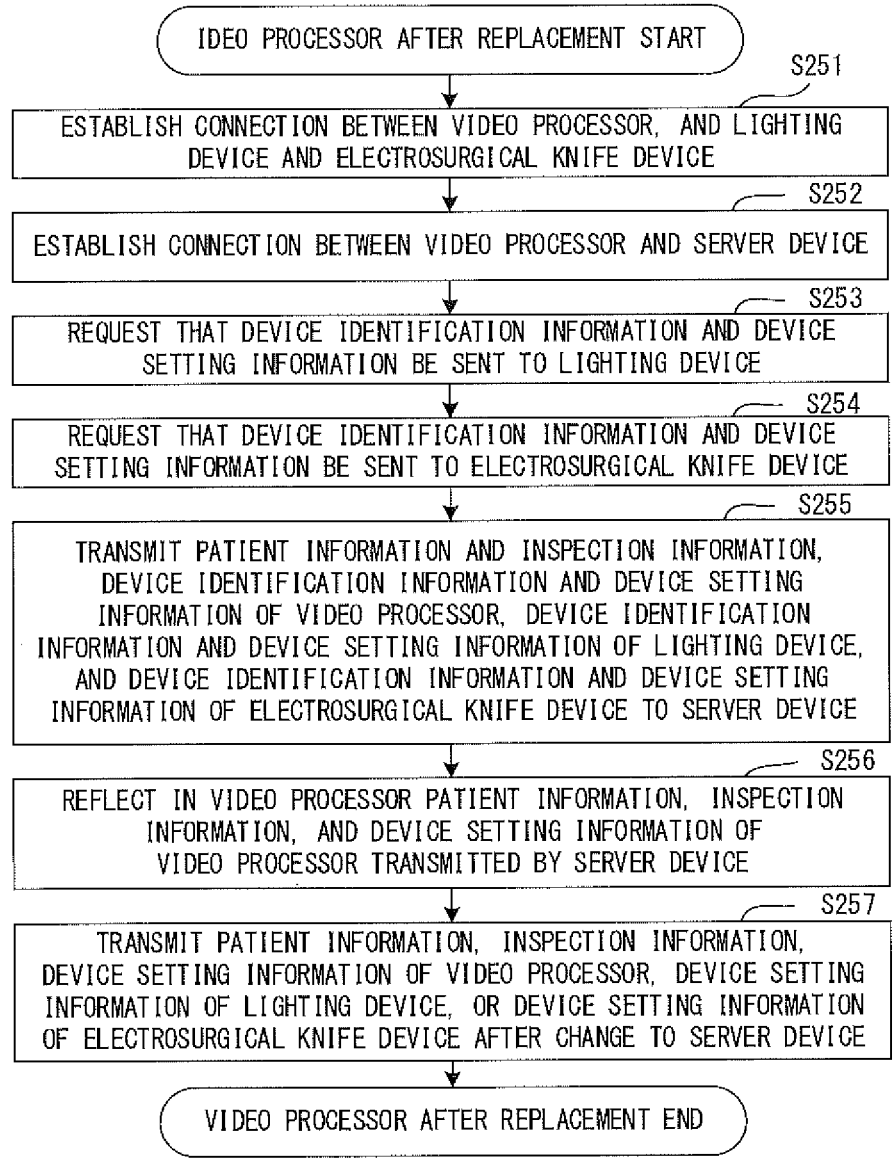
FIG. 22 illustrates an operation example of a video processor after the replacement.

FIG. 17 illustrates an operation example of the video processor 210*a* before the replacement. FIG. 18 illustrates an operation example of the lighting device 220. FIG. 19 illustrates an operation example of the electrosurgical knife device 230. FIG. 20 illustrates an operation example of the server device 240. FIG. 21 illustrates an operation example of the user (e.g., a doctor or a nurse). FIG. 22 illustrates an operation example of the video processor 210*b* after the replacement.

In this operation example, as illustrated in FIG. 17, the video processor 210*a* first turns ON a power supply, for example, in response to an operation of the user (S201 of FIG. 17).

Subsequently, the video processor 210*a* establishes a connection between the video processor 210*a*, and the lighting device 220 and the electrosurgical knife device 230 in which a power supply is turned ON (S202 of FIG. 17).

Subsequently, the video processor 210*a* establishes a connection between the video processor 210*a* and the server device 240 (S203 of FIG. 17).

Subsequently, the video processor 210*a* requests that the device identification information and the device setting information be transmitted to the lighting device 220 (S204 of FIG. 17).

After S204 of FIG. 17, as illustrated in FIG. 18, in response to the request, the lighting device 220 transmits the device identification information and the device setting information of the lighting device 220 to the video processor 210*a* (S211 of FIG. 18).

After S211 of FIG. 18, as illustrated in FIG. 17, the video processor 210*a* requests that the device identification information and the device setting information be transmitted to the electrosurgical knife device 230 (S205 of FIG. 17).

After S205 of FIG. 17, as illustrated in FIG. 19, in response to the request, the electrosurgical knife device 230 transmits the device identification information and the device setting information of the electrosurgical knife device 230 to the video processor 210*a* (S221 of FIG. 19).

After S221 of FIG. 19, as illustrated in FIG. 17, the video processor 210*a* transmits to the server device 240 the patient information and the inspection information stored in the storage unit 211, the device identification information and the device setting information of the video processor 210*a*, the device identification information and the device setting information of the lighting device 220 transmitted in S211 of FIG. 18 by the lighting device 220, and the device identification information and the device setting information of the electrosurgical knife device 230 transmitted in S221 of FIG. 19 by the electrosurgical knife device 230 (S206 of FIG. 17) (see the upper side of FIG. 16).

After S206 of FIG. 17, as illustrated in FIG. 20, the server device 240 stores the information transmitted in S206 of FIG. 17 by the video processor 210*a* in the storage unit 241, for example, by associating the pieces of information with each other as in the trolley information in the storage unit 241 of the upper side of FIG. 16 (S231 of FIG. 20).

After S231 of FIG. 20, as illustrated in FIG. 18, for example, when the device setting is changed by an operation of the user and the device setting information of the lighting device 220 is changed, the lighting device 220 transmits the device setting information after the change to the video processor 210*a* (S212 of FIG. 18).

After S212 of FIG. 18, as illustrated in FIG. 19, for example, when the device setting is changed by an operation of the user and the device setting information of the electrosurgical knife device 230 is changed, the electrosurgical knife device 230 transmits the device setting information after the change to the video processor 210*a* (S222 of FIG. 19).

After S222 of FIG. 19, as illustrated in FIG. 17, for example, when the patient information or the inspection information stored in the storage unit 211 is changed by an operation of the user, the video processor 210*a* transmits the patient information or the inspection information after the change to the server device 240 (S207 of FIG. 17). Alternatively, in S207 of FIG. 17, for example, when the device setting is changed by an operation of the user and the device setting information of the video processor 210*a* is changed, the video processor 210*a* transmits the device setting information after the change to the server device 240. Or, in S207 of FIG. 17, the video processor 210*a* transmits to the server device 240 the device setting information after the change of the lighting device 220 transmitted in S212 of FIG. 18 by the lighting device 220 or the device setting information after the change of the electrosurgical knife device 230 transmitted in S222 of FIG. 19 by the electrosurgical knife device 230.

After S207 of FIG. 17, as illustrated in FIG. 20, the server device 240 reflects the change information transmitted in S207 of FIG. 17 by the video processor 210*a* in the trolley information stored in the storage unit 241 and updates the trolley information (S232 of FIG. 20).

After S232 of FIG. 20, as illustrated in FIG. 21, the user starts an inspection (S241 of FIG. 21).

Assume in this operation example that after S241 of FIG. 21, the video processor 210*a* has failed as illustrated in FIG. 17 (S208 of FIG. 17). In this case, information relating to the failure of the video processor 210*a*, the location of the alternative medical device (the video processor 210*b*), or the like is reported to the user, for example, as described in the first embodiment.

After S208 of FIG. 17, as illustrated in FIG. 21, the user replaces the failed video processor 210*a* with the video processor 210*b* (S242 of FIG. 21).

After S242 of FIG. 21, as illustrated in FIG. 22, the video processor 210*b* after the replacement performs a process of S251 to S253. Since this process is the same process as that of S202 to S204 of FIG. 17, their explanation is omitted here.

After S253 of FIG. 22, as illustrated in FIG. 18, the lighting device 220 performs a process of S213. Since this process is the same process as that of S211, its explanation is omitted here.

After S213 of FIG. 18, as illustrated in FIG. 22, the video processor 210b performs a process of S254. Since this process is the same process as that of S205 of FIG. 17, its explanation is omitted here.

After S254 of FIG. 22, as illustrated in FIG. 19, the electrosurgical knife device 230 performs a process of S223. Since this process is the same process as that of S221, its explanation is omitted here.

After S223 of FIG. 19, as illustrated in FIG. 22, the video processor 210b performs a process of S255. Since this process is the same process as that of S206 of FIG. 17, its explanation is omitted here.

After S255 of FIG. 22, as illustrated in FIG. 20, the server device 240 compares the trolley information (the device identification information of each device of the video processor 210b, the lighting device 220, and the electrosurgical knife device 230) transmitted in S225 of FIG. 22 by the video processor 210b with the trolley configuration information (the device identification information of each device of the video processor 210a, the lighting device 220, and the electrosurgical knife device 230) stored in the storage unit 241. As a result, due to the fact that the device identification information of the video processor 210 is different, the server device 240 detects that the video processor 210 has been replaced (S233 of FIG. 20).

Subsequently, the server device 240 transmits to the video processor 210b the patient information, the inspection information, and the device setting information of the video processor 210 (i.e., the video processor 210a before the replacement) in the trolley information stored in the storage unit 241 (S234 of FIG. 20) (see the lower side of FIG. 16).

After S234 of FIG. 20, the video processor 210b reflects in the video processor 210b the patient information, the inspection information, and the device setting information of the video processor 210a transmitted in S234 of FIG. 20 by the server device 240 (S256 of FIG. 22). That is, the video processor 210b stores the patient information and the inspection information of the video processor 210a in the storage unit 211 of the video processor 210b, and performs the device setting of the video processor 210b in accordance with the device setting information of the video processor 210a. Thereby, a state of the video processor 210b after the replacement is restored to that of the video processor 210a before the replacement.

After S256 of FIG. 22, as illustrated in FIG. 18, the lighting device 220 performs a process of S214. Since this process is the same process as that of S212, its explanation is omitted here.

After S214 of FIG. 18, as illustrated in FIG. 19, the electrosurgical knife device 230 performs a process of S224. Since this process is the same process as that of S222, its explanation is omitted here.

After S224 of FIG. 19, as illustrated in FIG. 22, the video processor 210b performs a process of S257. Since this process is the same process as that of S207 of FIG. 17, its explanation is omitted here.

After S257 of FIG. 22, as illustrated in FIG. 20, the server device 240 performs a process of S235. Since this process is the same process as that of S232, its explanation is omitted here.

As described above, when S208 of FIG. 17, S214 of FIG. 18, S224 of FIG. 19, S235 of FIG. 20, S242 of FIG. 21, and S257 of FIG. 22 end, the operation example of the medical system 200 according to the present embodiment is completed.

As described above, according to the medical system 200 of the present embodiment, when the replacement of the video processor 210 is performed due to a failure or the like, the state (the patient information, the inspection information, and the device setting) of the video processor 210b after the replacement can be automatically restored to that of the video processor 210a before the replacement. Further, when the replacement of the peripheral device (the lighting device 220 or the electrosurgical knife device 230) is performed due to a failure or the like, the state (the device setting) of the peripheral device after the replacement can be automatically restored to that of the peripheral device before the replacement in the same way. Thereby, as in the conventional case, the user does not require a re-input of the patient information and the inspection information for the device (the video processor) after the replacement, or resetting of the devices (the video processor, the lighting device, and the electrosurgical knife device) after the replacement, and a burden on the user caused by the device replacement can be reduced. Further, even if the device replacement is performed during the inspection, the inspection before the replacement and the inspection after the replacement can be treated as the same inspection, and therefore the inspection can be continued. Accordingly, as in the conventional case, the inspection is not interrupted for the device replacement during the inspection, and the inspection before the replacement and the inspection after the replacement are not treated as different inspections.

In the medical system 200 according to the present embodiment, various kinds of deformation are possible.

In the medical system 200 according to the present embodiment, for example, in addition to the trolley 250 on which the video processor 210, the lighting device 220, and the electrosurgical knife device 230 are mounted, a plurality of trolleys on which a plurality of the medical devices are mounted may be provided. In this case, for example, the server device 240 may store the trolley information in the storage unit 241 for each trolley.

Third Embodiment

FIG. 23 illustrates a configuration example of a medical system according to a third embodiment of the present invention.

In FIG. 23, an upper side illustrates a configuration including a video processor before a replacement and a lower side illustrates a configuration including a video processor after the replacement.

As illustrated at the upper side and the lower side of FIG. 23, the medical system 300 according to the present embodiment has a configuration that includes a video processor 310 (a video processor 310a before the replacement or a video processor 310b after the replacement), a lighting device 320, and an electrosurgical knife device 330, and in which the lighting device 320 and the electrosurgical knife device 330 are connected to the video processor 310. Further, the video processor 310, the lighting device 320, and the electrosurgical knife device 330 are mounted on a trolley 340.

The medical system 300 according to the present embodiment is, for example, a part of the medical system 100 according to the first embodiment. In this case, for example, the video processor 310 corresponds to the video processor 20, the lighting device 320 corresponds to the peripheral device 40, and the electrosurgical knife device 330 corresponds to the peripheral device 50.

In the medical system 300 according to the present embodiment, the video processor 310 includes a storage unit 311, a portable memory 312 that is freely attached to or detached from the video processor 310, an updating unit 313, and a comparison unit 314.

In the storage unit 311, patient information relating to a patient, inspection information relating to an inspection, and the like are stored.

The portable memory 312 is, for example, a USB (Universal Serial Bus) memory or the like, and in the portable memory 312, the patient information and the inspection information stored in the storage unit 311, device identification information and device setting information of the video processor 310, device identification information and device setting information of the peripheral devices (the lighting device 320 and the electrosurgical knife device 330) connected to the video processor 310, and the like are stored by being associated with each other as trolley information. Further, the device identification information and the device setting information of the peripheral devices (the lighting device 320 and the electrosurgical knife device 330) are acquired from the peripheral devices by the video processor 310. Further, hereinafter, the device identification information of the devices (the video processor 310, the lighting device 320, and the electrosurgical knife device 330) that is mounted on the trolley 340 is also referred to as trolley configuration information.

The updating unit 313 updates corresponding information stored in the portable memory 312 in response to a change in the patient information or the inspection information stored in the storage unit 311, a change in the device setting of the video processor 310, or the device setting information after a change in the peripheral devices acquired from the peripheral devices (the lighting device 320 or the electrosurgical knife device 330).

The comparison unit 314 compares the device identification information of the video processor 310 and the device identification information of the peripheral devices acquired from the peripheral devices (the lighting device 320 and the electrosurgical knife device 330) with the device identification information of the video processor 310 stored in the portable memory 312 and the device identification information of the peripheral devices (the lighting device 320 and the electrosurgical knife device 330).

In the medical system 300 according to the present embodiment, as described below in detail with reference to FIGS. 24 to 28, as a result of the comparison by the comparison unit 314, when the device identification information of the video processor 310 is different, it is recognized that the video processor 310 has been replaced. Further, the video processor 310 (310b) stores in the storage unit 311 of the video processor 310 (310b) the patient information and the inspection information stored in the portable memory 312 (the portable memory 312 replaced with the video processor 310b from the video processor 310a). Further, the video processor 310 (310b) performs the device setting of the video processor 310 (310b) in accordance with the device setting information of the video processor 310 (310a) stored in the portable memory 312.

Although it is not described in detail, as a result of the comparison by the comparison unit 314, when the pieces of device identification information of the peripheral devices (the lighting device 320 and the electrosurgical knife device 330) are different from each other, the video processor 310 performs the device setting of the peripheral device (the peripheral device after the replacement) in accordance with the device setting information of the peripheral device (the peripheral device before the replacement) stored in the portable memory 312.

Next, an operation example of the medical system 300 according to the present embodiment will be described.

Herein, an operation example of the case in which the replacement of the video processor 310 is performed due to a failure of the video processor 310 will be described as the operation example.

To facilitate understanding of the above, in this explanation, an operation example of a user (e.g., a doctor or a nurse) as well as operation examples of the video processor 310a before the replacement, the video processor 310b after the replacement, the lighting device 320, and the electrosurgical knife device 330 will be described.

Figure 24:
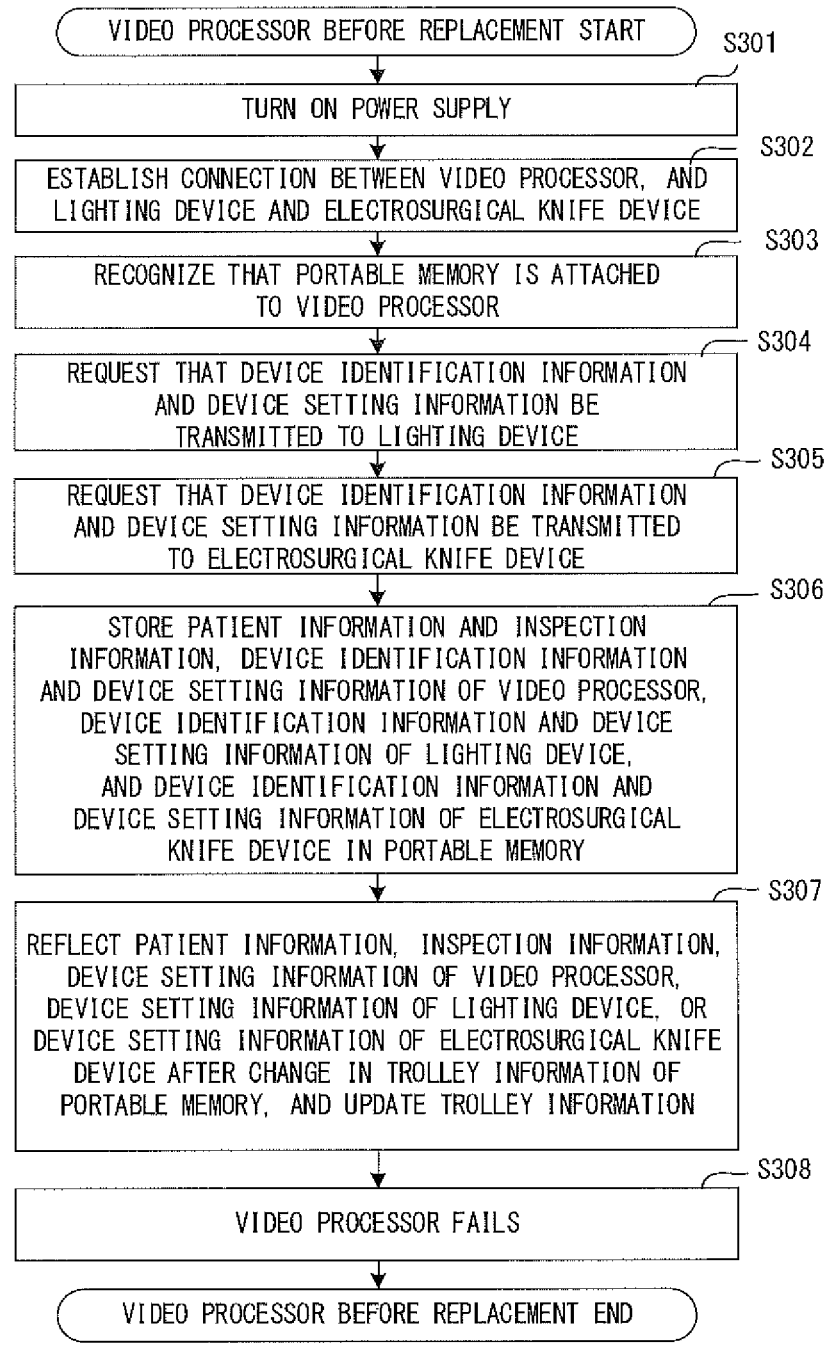
FIG. 24 illustrates an operation example of a video processor before a replacement.
Figure 25:
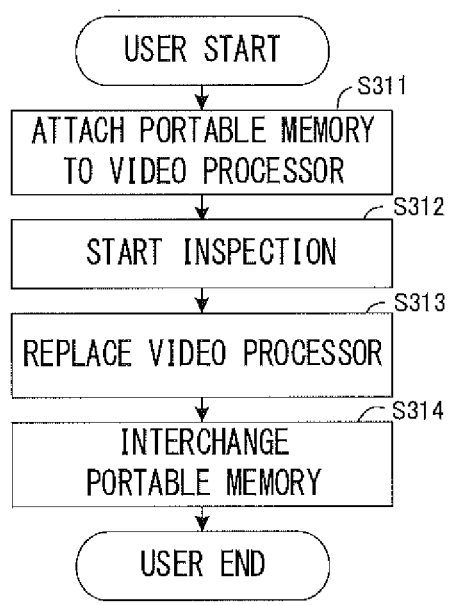
FIG. 25 illustrates an operation example of a user (e.g., a doctor or a nurse).
Figure 26:
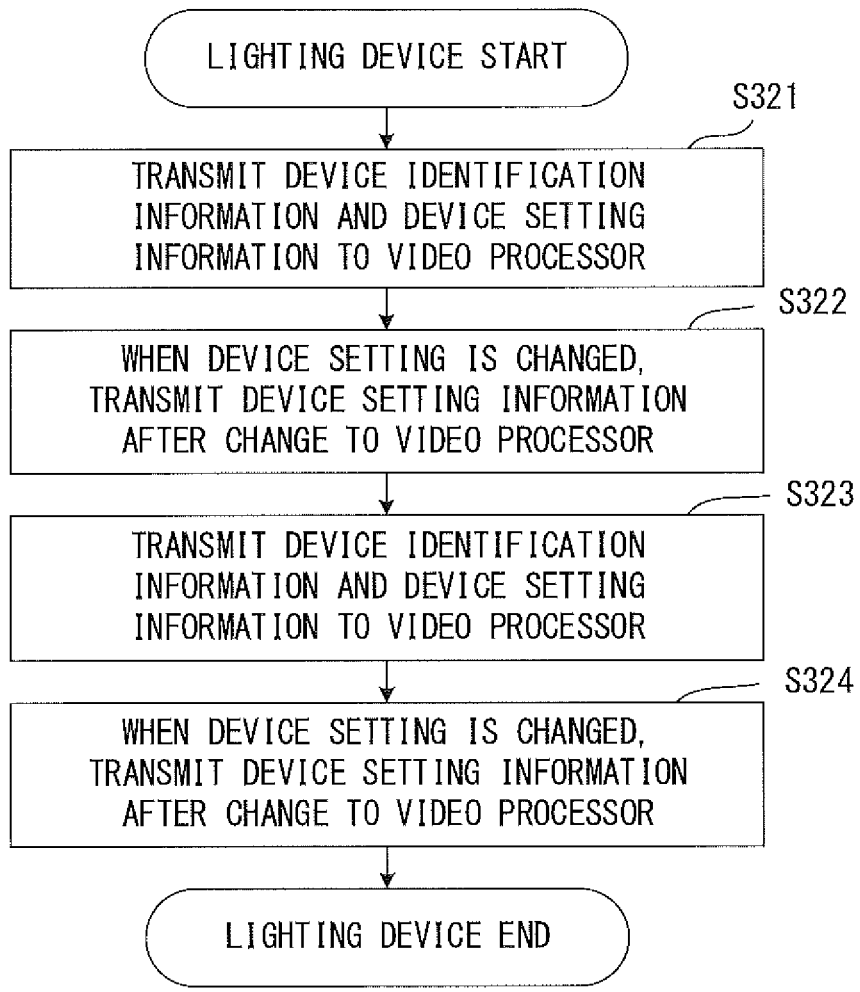
FIG. 26 illustrates an operation example of a lighting device.
Figure 27:
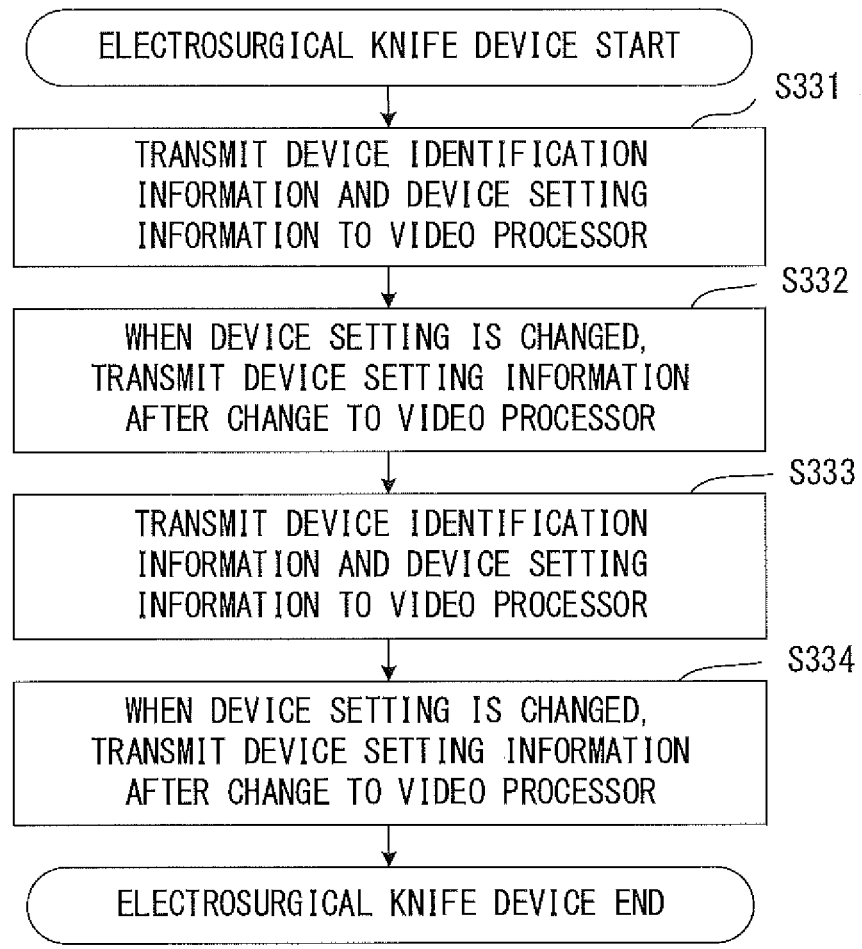
FIG. 27 illustrates an operation example of an electrosurgical knife device.
Figure 28:
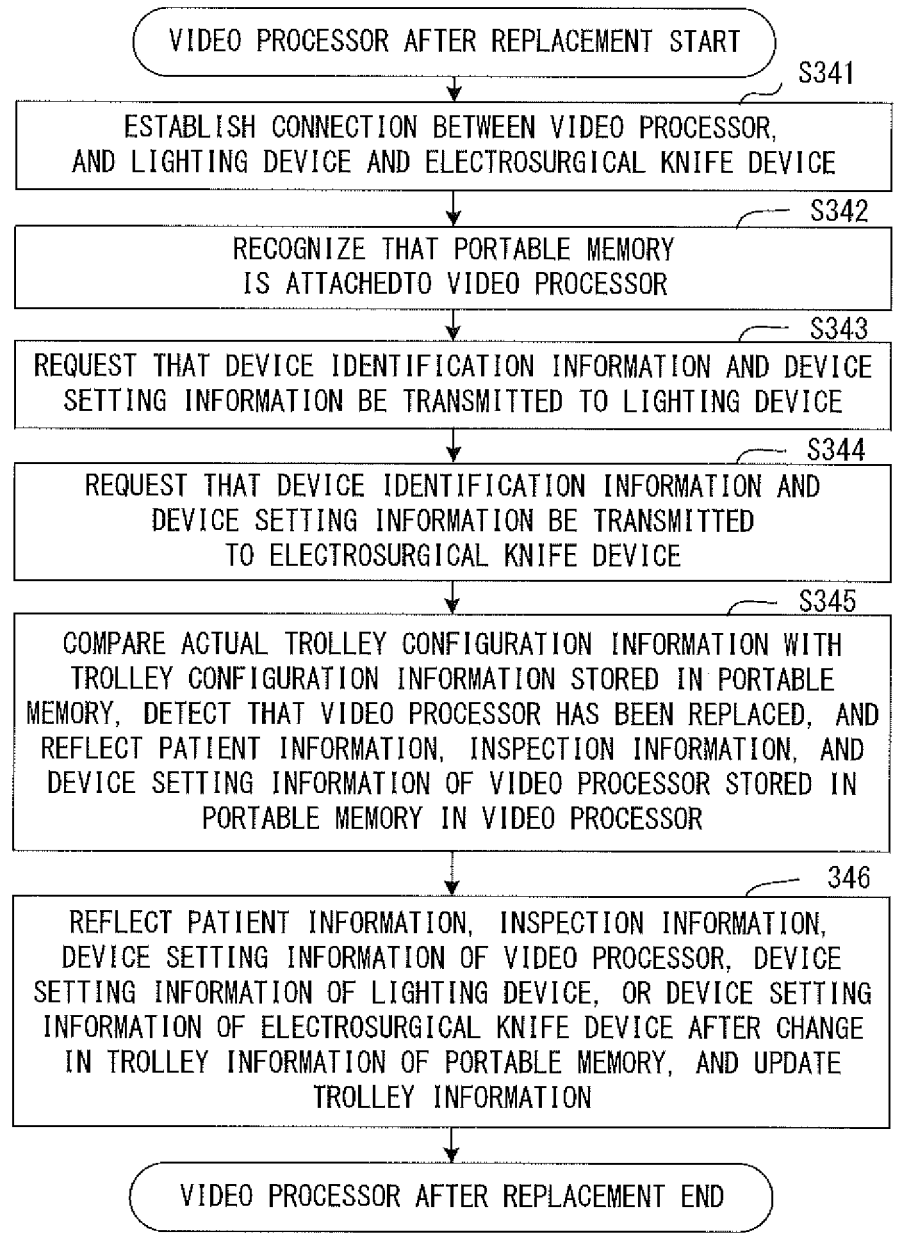
FIG. 28 illustrates an operation example of a video processor after the replacement.

FIG. 24 illustrates an operation example of the video processor 310a before the replacement. FIG. 25 illustrates an operation example of the user (e.g., a doctor or a nurse). FIG. 26 illustrates an operation example of the lighting device 320. FIG. 27 illustrates an operation example of the electrosurgical knife device 330. FIG. 28 illustrates an operation example of the video processor 310b after the replacement.

In this operation example, as illustrated in FIG. 24, the video processor 310a first turns ON a power supply, for example, in response to an operation of the user (S301 of FIG. 24).

Subsequently, the video processor 310a establishes a connection between the video processor 310a, and the lighting device 320 and the electrosurgical knife device 330 in which a power supply is turned ON (S302 of FIG. 24).

After S302 of FIG. 24, as illustrated in FIG. 25, the user attaches the portable memory 312 to the video processor 310a (S311 of FIG. 25). At this point in time, no trolley information is assumed to be stored in the portable memory 312.

After S311 of FIG. 25, as illustrated in FIG. 24, the video processor 310a recognizes that the portable memory 312 is attached thereto (S303 of FIG. 24).

Subsequently, the video processor 310a requests that the device identification information and the device setting information be transmitted to the lighting device 320 (S304 of FIG. 24).

After S304 of FIG. 24, as illustrated in FIG. 26, in response to the request, the lighting device 320 transmits the device identification information and the device setting information of the lighting device 320 to the video processor 310a (S321 of FIG. 26).

After S321 of FIG. 26, as illustrated in FIG. 24, the video processor 310a requests that the device identification information and the device setting information be transmitted to the electrosurgical knife device 330 (S305 of FIG. 24).

After S305 of FIG. 24, as illustrated in FIG. 27, in response to the request, the electrosurgical knife device 330 transmits the device identification information and the device setting information of the electrosurgical knife device 330 to the video processor 310a (S331 of FIG. 27).

After S331 of FIG. 27, as illustrated in FIG. 24, the video processor 310a stores in the portable memory 312 the patient information and the inspection information stored in the storage unit 311, the device identification information and the device setting information of the video processor 310a, the device identification information and the device setting information of the lighting device 320 transmitted in S321 of FIG. 26 by the lighting device 320, and the device identification information and the device setting information of the electrosurgical knife device 330 transmitted in S331 of FIG. 27 by the electrosurgical knife device 330, for example, by associating the pieces of information with each other as in the trolley information in the portable memory 312 of the upper side of FIG. 23 (S306 of FIG. 24).

After S306 of FIG. 24, as illustrated in FIG. 25, the user starts an inspection (S312 of FIG. 25).

After S312 of FIG. 25, as illustrated in FIG. 26, for example, when the device setting is changed by an operation of the user and the device setting information of the lighting device 320 is changed, the lighting device 320 transmits the device setting information after the change to the video processor 310a (S322 of FIG. 26).

After S322 of FIG. 26, as illustrated in FIG. 27, for example, when the device setting is changed by an operation of the user and the device setting information of the electrosurgical knife device 330 is changed, the electrosurgical knife device 330 transmits the device setting information after the change to the video processor 310a (S332 of FIG. 27).

After S332 of FIG. 27, as illustrated in FIG. 24, for example, when the patient information or the inspection information stored in the storage unit 311 is changed by an operation of the user, the video processor 310a reflects the patient information or the inspection information after the change in the trolley information of the portable memory 312, and updates the trolley information (S307 of FIG. 24). Alternatively, in S307 of FIG. 24, for example, when the device setting is changed by an operation of the user and the device setting information of the video processor 310a is changed, the video processor 310a reflects the device setting information after the change in the trolley information of the portable memory 312, and updates the trolley information. Or, in S307 of FIG. 24, the video processor 310a reflects the device setting information after the change of the lighting device 320 transmitted in S322 of FIG. 26 by the lighting device 320 or the device setting information after the change of the electrosurgical knife device 330 transmitted in S332 of FIG. 27 by the electrosurgical knife device 330 in the trolley information of the portable memory 312, and updates the trolley information.

Assume in this operation example that after S307 of FIG. 24, the video processor 310a has failed as illustrated in FIG. 24 (S308 of FIG. 24). In this case, information relating to the failure of the video processor 310a, the location of the alternative medical device thereof (the video processor 310b), or the like is reported to the user, for example, as described in the first embodiment.

After S308 of FIG. 24, as illustrated in FIG. 25, the user replaces the failed video processor 310a with the video processor 310b (S313 of FIG. 25).

After S313 of FIG. 25, as illustrated in FIG. 28, the video processor 310b performs a process of S341. Since this process is the same process as that of S302 of FIG. 24, its explanation is omitted here.

After S341 of FIG. 28, as illustrated in FIG. 25, the user attaches the portable memory 312 attached to the video processor 310a to the video processor 310b (S314 of FIG. 25). That is, the user interchanges the portable memory 312 from the video processor 310a to the video processor 310b.

After S314 of FIG. 25, as illustrated in FIG. 28, the video processor 310b performs a process of S342 and S343. Since this process is the same process as that of S303 and S304 of FIG. 24, their explanation is omitted here.

After S343 of FIG. 28, as illustrated in FIG. 26, the lighting device 320 performs a process of S323. Since this process is the same process as that of S321, its explanation is omitted here.

After S323 of FIG. 26, as illustrated in FIG. 28, the video processor 310b performs a process of S344. Since this process is the same process as that of S305 of FIG. 24, its explanation is omitted here.

After S344 of FIG. 28, as illustrated in FIG. 27, the electrosurgical knife device 330 performs a process of S333. Since this process is the same process as that of S331, its explanation is omitted here.

After S333 of FIG. 27, as illustrated in FIG. 28, the video processor 310b compares the trolley configuration information (the device identification information of each device of the video processor 310b, the lighting device 320, and the electrosurgical knife device 330) at this time, with the trolley configuration information (the device identification information of each device of the video processor 310a, the lighting device 320, and the electrosurgical knife device 330) stored in the portable memory 312. As a result, due to the fact that the device identification information of the video processor 310 is different, the video processor 310b detects that the video processor 310 has been replaced, and reflects the patient information, the inspection information, and the device setting information of the video processor 310a in the trolley information stored in the portable memory 312 in the video processor 310b (S345 of FIG. 28). That is, the video processor 310b stores the patient information and the inspection information of the video processor 310a in the storage unit 311 of the video processor 310b, and performs the device setting of the video processor 310b in accordance with the device setting information of the video processor 310a. Thereby, a state of the video processor 310b after the replacement is restored to that of the video processor 310a before the replacement.

After S345 of FIG. 28, as illustrated in FIG. 26, the lighting device 320 performs a process of S324. Since this process is the same process as that of S322, its explanation is omitted here.

After S324 of FIG. 26, as illustrated in FIG. 27, the electrosurgical knife device 330 performs a process of S334. Since this process is the same process as that of S332, its explanation is omitted here.

After S334 of FIG. 27, as illustrated in FIG. 28, the video processor 310b performs a process of S346. Since this process is the same process as that of S307 of FIG. 24, its explanation is omitted here.

As described above, when S308 of FIG. 24, S314 of FIG. 25, S324 of FIG. 26, S334 of FIG. 27, and S346 of FIG. 28 end, the operation example of the medical system 300 according to the present embodiment is completed.

As described above, according to the medical system 300 of the present embodiment, when the replacement of the video processor 310 is performed due to the failure or the like, the user only interchanges the portable memory 312 from the video processor 310a before the replacement to the video processor 310b after the replacement to thereby restore the state (the patient information, the inspection information, and the device setting) of the video processor 310b after the replacement to that of the video processor 310a before the replacement automatically. Further, when the replacement of the peripheral device (the lighting device 320 or the electrosurgical knife device 330) is performed due to the failure or the like, the user can automatically restore the state (the device setting) of the peripheral device after the replacement to that of the peripheral device before the replacement. Thereby, as in the conventional case, the user does not require a re-input of the patient information and the inspection information for the device (the video processor) after the replacement, or resetting of the devices (the video processor, the lighting device, and the electrosurgical knife device) after the replacement, and a burden on the user caused by the device replacement can be reduced. Further, even if the device replacement is performed during the inspection, the inspection before the replacement and the inspection after the replacement can be treated as the same inspection, and therefore the inspection can be continued. Accordingly, as in the conventional case, the inspection is not interrupted due to the device replacement during the inspection, and the inspection before the replacement and the inspection after the replacement are not treated as different inspections.

In the medical system 300 according to the present embodiment, various kinds of deformation are possible.

In the medical system 300 according to the present embodiment, for example, in addition to the trolley 340 on which the video processor 310, the lighting device 320, and the electrosurgical knife device 330 are mounted, a plurality of trolleys may be provided on which a plurality of the medical devices are mounted. In this case, for example, the video processor 310 may store the trolley information in the portable memory 312 for each trolley.

Fourth Embodiment

Figure 29:
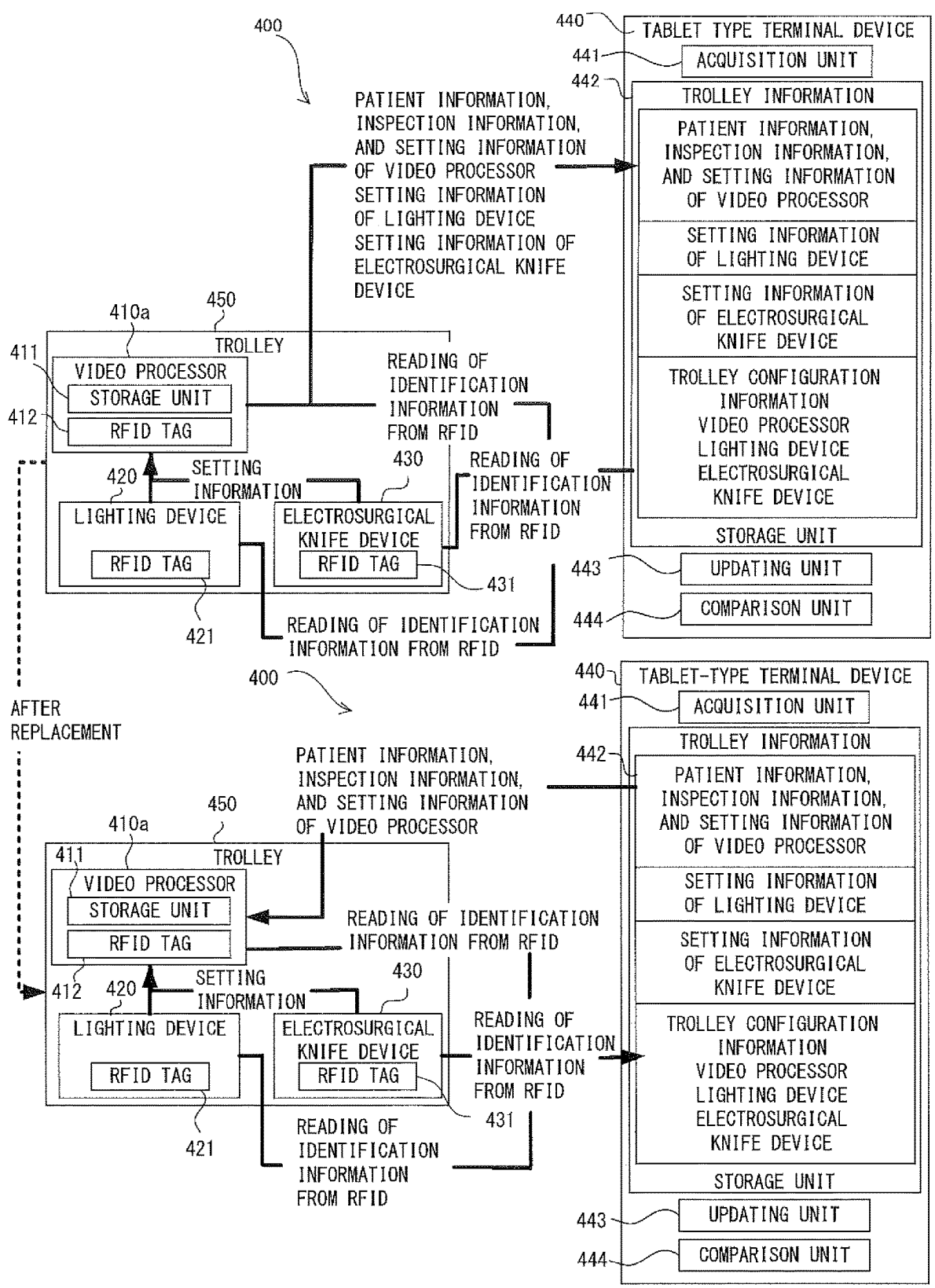
FIG. 29 illustrates a configuration example of a medical system according to a fourth embodiment.

FIG. 29 illustrates a configuration example of a medical system according to a fourth embodiment of the present invention.

In FIG. 29, an upper side illustrates a configuration including a video processor before a replacement and a lower side illustrates a configuration including a video processor after the replacement.

As illustrated at the upper side or the lower side of FIG. 29, the medical system 400 according to the present embodiment has a configuration that includes a video processor 410 (a video processor 410a before the replacement or a video processor 410b after the replacement), a lighting device 420, an electrosurgical knife device 430, and a tablet-type terminal device 440, and in which the lighting device 420 and the electrosurgical knife device 430 are connected (e.g., wired-connected) to the video processor 410 and the video processor 410 is connected (e.g., wirelessly connected) to the tablet-type terminal device 440 via a network (not illustrated). Further, the video processor 410, the lighting device 420, and the electrosurgical knife device 430 are mounted on a trolley 450.

The medical system 400 according to the present embodiment is, for example, a part of the medical system 100 according to the first embodiment. In this case, for example, the video processor 410 corresponds to the video processor 20, the lighting device 420 corresponds to the peripheral device 40, and the electrosurgical knife device 430 corresponds to the peripheral device 50.

In the medical system 400 according to the present embodiment, the video processor 410 includes a storage unit 411 and an RFID (Radio Frequency IDentification) tag 412.

In the storage unit 411, patient information relating to a patient, inspection information relating to an inspection, and the like are stored.

The RFID tag 412 stores device identification information or the like of the video processor 410.

Further, the video processor 410 transmits to the tablet-type terminal device 440 one or more of the patient information stored in the storage unit 411, the inspection information stored in the storage unit 411, device setting information of the video processor 410, and device setting information of the peripheral devices (the lighting device 420 and the electrosurgical knife device 430) connected to the video processor 410. Device identification information of the lighting device 420 is acquired from the lighting device 420 by the video processor 410. Further, device setting information of the electrosurgical knife device 430 is acquired from the electrosurgical knife device 430 by the video processor 410.

The lighting device 420 includes an RFID tag 421.

The RFID tag 421 stores the device identification information or the like of the lighting device 420.

The electrosurgical knife device 430 includes an RFID tag 431.

The RFID tag 431 stores the device identification information or the like of the electrosurgical knife device 430.

The tablet-type terminal device 440 is an example of a portable terminal device, and includes an acquisition unit 441, a storage unit 442, an updating unit 443, and a comparison unit 444.

The acquisition unit 441 is a reader-writer for performing reading of information from the RFID tag and writing of information to the RFID tag, and reads out the device identification information of each device, for example, from the RFID tag 412 of the video processor 410, the RFID tag 421 of the lighting device 420, and the RFID tag 431 of the electrosurgical knife device 430.

In the storage unit 442, the patient information and the inspection information stored in the storage unit 411 of the video processor 410, the device identification information and the device setting information of the video processor 410, the device identification information and the device setting information of the peripheral devices (the lighting device 420 and the electrosurgical knife device 430) connected to the video processor 410, and the like are stored by being associated with each other as the trolley information. Hereinafter, the device identification information of the devices (the video processor 410, the lighting device 420, and the electrosurgical knife device 430) mounted on the trolley 450 is also referred to as the trolley configuration information.

The updating unit 443 updates corresponding information stored in the storage unit 442 in response to the patient information, the inspection information, the device setting information of the video processor 410, or the device setting information of the peripheral device (the lighting device 420 or the electrosurgical knife device 430), after the change, transmitted by the video processor 410.

The comparison unit 444 compares the device identification information of the video processor 410 and the device identification information of the peripheral devices (the lighting device 420 and the electrosurgical knife device 430) acquired by the acquisition unit 441 with the device identification information of the video processor 410 and the device identification information of the peripheral devices (the lighting device 420 and the electrosurgical knife device 430) stored in the storage unit 442.

In the medical system 400 according to the present embodiment, as described below in detail with reference to FIGS. 30 to 35, as a result of the comparison by the comparison unit 444, when the device identification information of the video processor 410 is different, it is recognized that the video processor 410 has been replaced. Further, the tablet-type terminal device 440 transmits to the video processor 410 (410b) the patient information, the inspection information, and the device setting information of the video processor 410 (410a) stored in the storage unit 442. Further, the video processor 410 (410b) stores the patient information and the inspection information transmitted by the tablet-type terminal device 440 in the storage unit 411 of the video processor 410 (410b). Further, the video processor 410 (410b) performs the device setting of the video processor 410 (410b) in accordance with the device setting information of the video processor 410 (410a) transmitted by the tablet-type terminal device 440.

Although it is not described in detail, as a result of the comparison by the comparison unit 444, when the device identification information of the peripheral device (the lighting device 420 or the electrosurgical knife device 430) is different, it is recognized that the peripheral device has been replaced. Further, the tablet-type terminal device 440 transmits to the video processor 410 the device setting information of the peripheral device (the peripheral device before the replacement) stored in the storage unit 442. Further, the video processor 410 performs the device setting of the peripheral device (the peripheral device after the replacement) in accordance with the device setting information of the peripheral device (the peripheral device before the replacement) transmitted by the tablet-type terminal device 440.

Next, an operation example of the medical system 400 according to the present embodiment will be described.

Herein, an operation example of the case in which the replacement of the video processor 410 is performed due to a failure of the video processor 410 will be described as the operation example.

To facilitate understanding of the above, in this explanation, an operation example of a user (e.g., a doctor or a nurse) as well as operation examples of the video processor 410a before the replacement, the video processor 410b after the replacement, the lighting device 420, the electrosurgical knife device 430, and the tablet-type terminal device 440 will be described.

Figure 30:
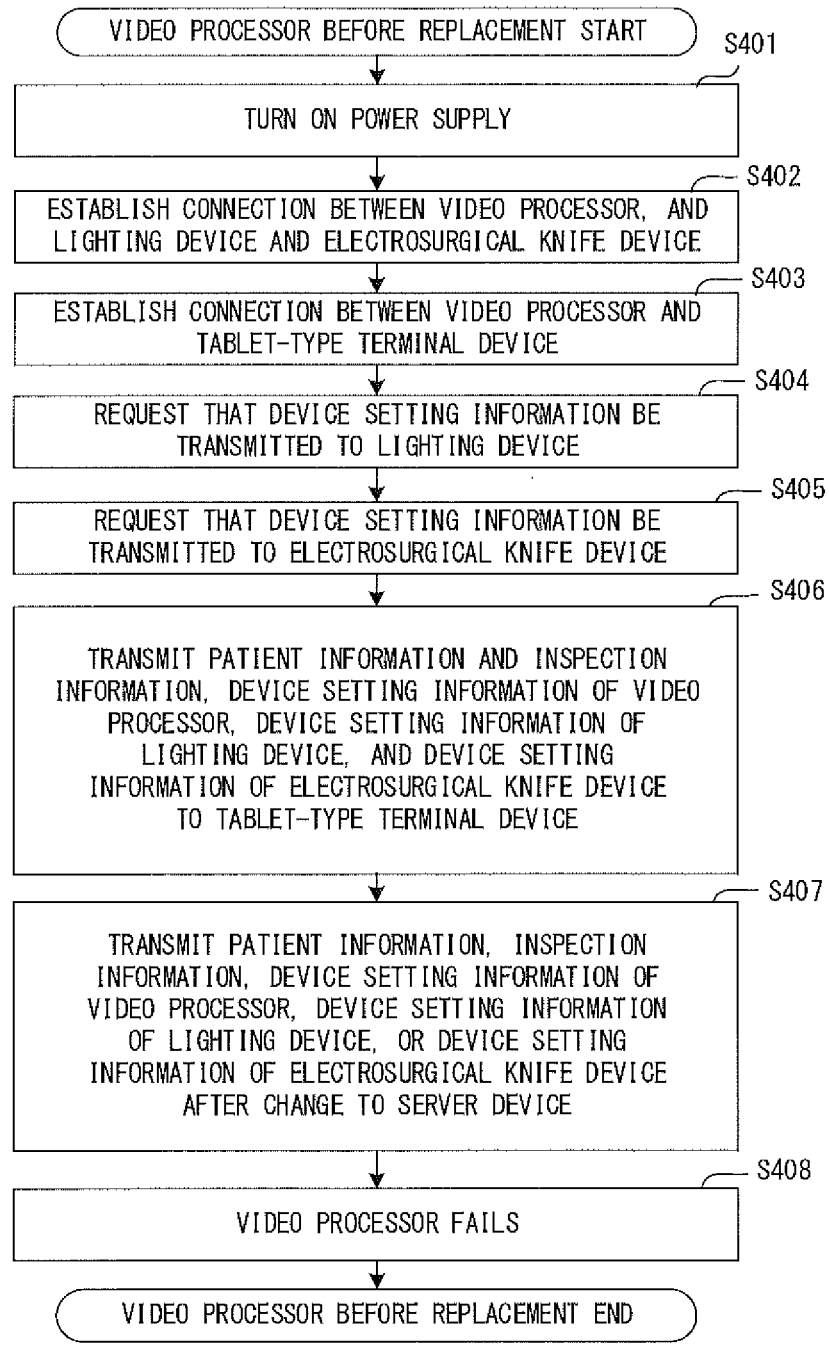
FIG. 30 illustrates an operation example of a video processor before a replacement.
Figure 32:
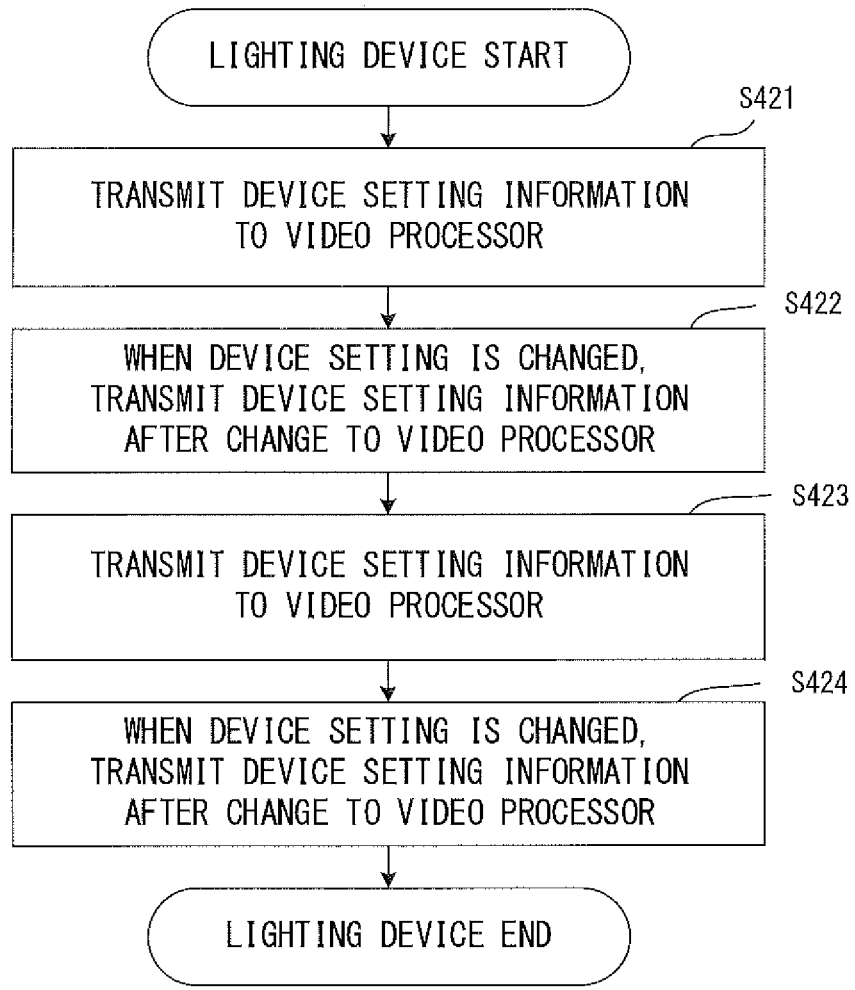
FIG. 32 illustrates an operation example of a lighting device.
Figure 33:
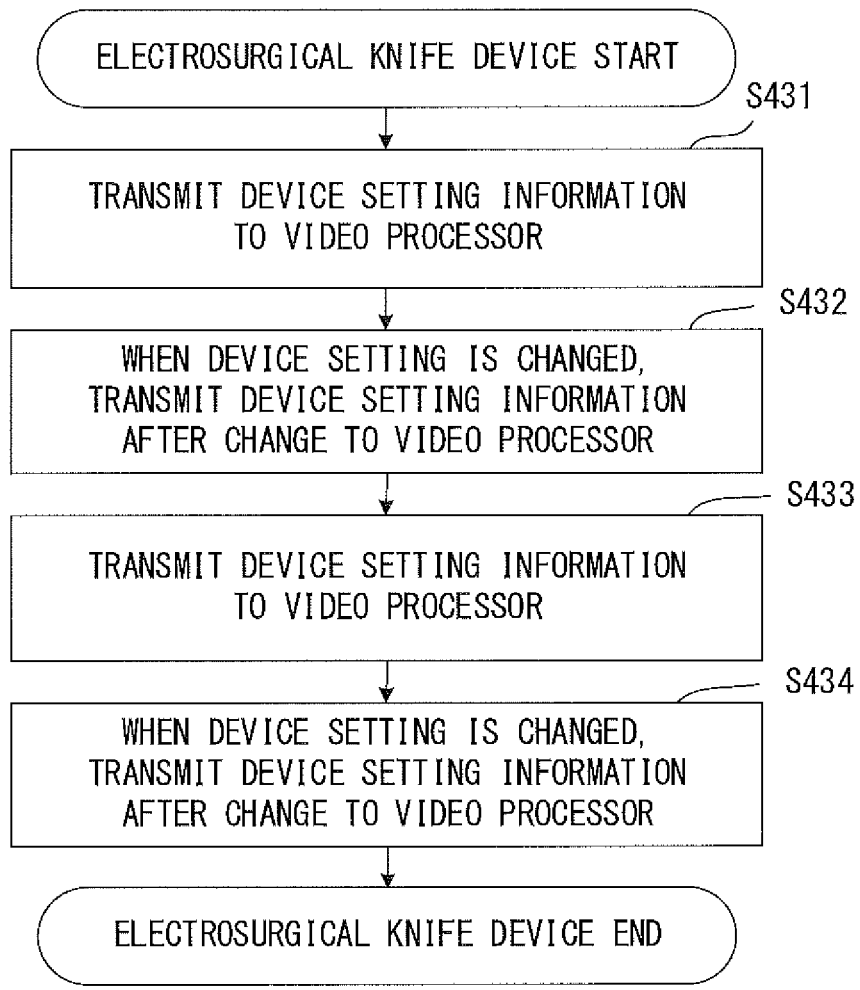
FIG. 33 illustrates an operation example of an electrosurgical knife device.
Figure 34:
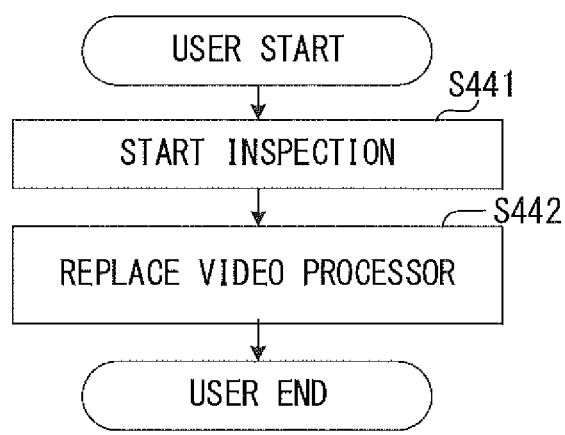
FIG. 34 illustrates an operation example of a user (e.g., a doctor or a nurse).
Figure 35:
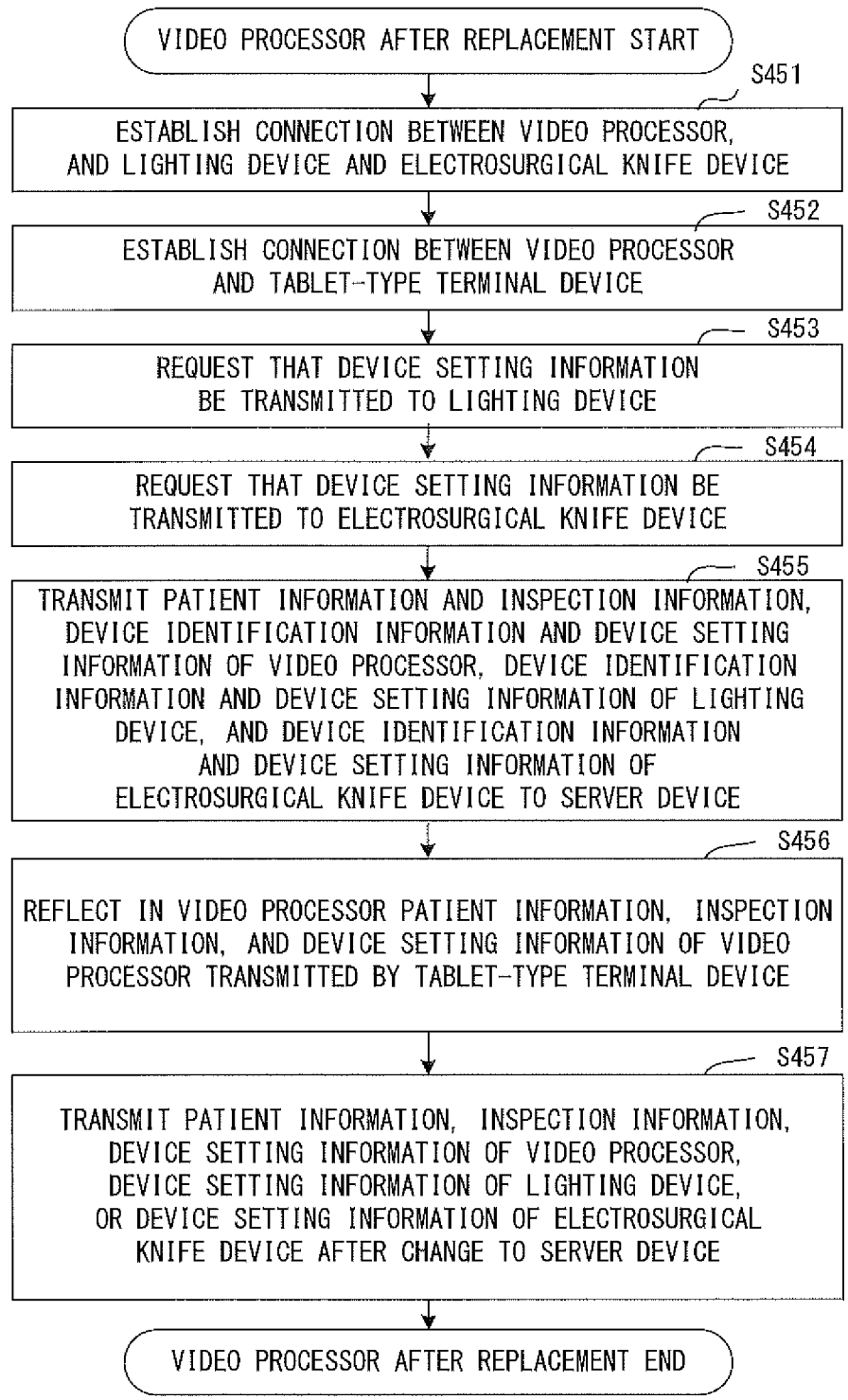
FIG. 35 illustrates an operation example of a video processor after the replacement.

FIG. 30 illustrates an operation example of the video processor 410a before the replacement. FIG. 31 illustrates an operation example of the tablet-type terminal device 440. FIG. 32 illustrates an operation example of the lighting device 420. FIG. 33 illustrates an operation example of the electrosurgical knife device 430. FIG. 34 illustrates an operation example of the user (e.g., a doctor or a nurse). FIG. 35 illustrates an operation example of the video processor 410b after the replacement.

In this operation example, as illustrated in FIG. 30, the video processor 410a first turns ON a power supply, for example, in response to an operation of the user (S401 of FIG. 30).

After S401 of FIG. 30, as illustrated in FIG. 31, the tablet-type terminal device 440 reads out the device identification information from each of the RFID tag 412 of the video processor 410, the RFID tag 421 of the lighting device 420, and the RFID tag 431 of the electrosurgical knife device 430, and stores the device identification information in the storage unit 442 as the trolley configuration information (S411 of FIG. 31) (see the upper side of FIG. 29).

After S411 of FIG. 31, the video processor 410a establishes a connection between the video processor 410a, and the lighting device 420 and the electrosurgical knife device 430 in which the power supply is turned ON (S402 of FIG. 30).

Subsequently, the video processor 410a establishes a connection between the video processor 410a and the tablet-type terminal device 440 (S403 of FIG. 30).

Subsequently, the video processor 410a requests that the device setting information be transmitted to the lighting device 420 (S404 of FIG. 30).

After S404 of FIG. 30, as illustrated in FIG. 32, in response to the request, the lighting device 420 transmits the device setting information of the lighting device 420 to the video processor 410a (S421 of FIG. 32).

After S421 of FIG. 32, as illustrated in FIG. 30, the video processor 410a requests that the device setting information be transmitted to the electrosurgical knife device 430 (S405 of FIG. 30).

After S405 of FIG. 30, as illustrated in FIG. 33, in response to the request, the electrosurgical knife device 430 transmits the device setting information of the electrosurgical knife device 430 to the video processor 410a (S431 of FIG. 33).

After S431 of FIG. 33, as illustrated in FIG. 30, the video processor 410a transmits to the tablet-type terminal device 440 the patient information and the inspection information stored in the storage unit 411, the device setting information of the video processor 410a, the device setting information of the lighting device 420 transmitted in S421 of FIG. 32 by the lighting device 420, and the device setting information of the electrosurgical knife device 430 transmitted in S431 of FIG. 33 by the electrosurgical knife device 430 (S406 of FIG. 30) (see the upper side of FIG. 29).

After S406 of FIG. 30, as illustrated in FIG. 31, the tablet-type terminal device 440 stores in the storage unit 442 the information transmitted in S406 of FIG. 30 by the video processor 410a with the trolley configuration information previously stored in S411, for example, by associating the pieces of information with each other as in the trolley information in the storage unit 442 of the upper side of FIG. 29 (S412 of FIG. 31).

After S412 of FIG. 31, as illustrated in FIG. 34, the user starts an inspection (S441 of FIG. 34).

After S441 of FIG. 34, as illustrated in FIG. 32, for example, when the device setting is changed by an operation of the user and the device setting information of the lighting device 420 is changed, the lighting device 420 transmits the device setting information after the change to the video processor 410a (S422 of FIG. 32).

After S422 of FIG. 32, as illustrated in FIG. 33, for example, when the device setting is changed by an operation of the user and the device setting information of the electrosurgical knife device 430 is changed, the electrosurgical knife device 430 transmits the device setting information after the change to the video processor 410a (S432 of FIG. 33).

After S432 of FIG. 33, as illustrated in FIG. 30, for example, when the patient information or the inspection information stored in the storage unit 411 is changed by an operation of the user, the video processor 410a transmits the patient information or the inspection information after the change to the tablet-type terminal device 440 (S407 of FIG. 30). Alternatively, in S407 of FIG. 30, for example, when the device setting is changed by an operation of the user and the device setting information of the video processor 410a is changed, the video processor 410a transmits the device setting information after the change to the tablet-type terminal device 440. Or, in S407 of FIG. 30, the video processor 410a transmits to the tablet-type terminal device 440 the device setting information after the change of the lighting device 420 transmitted in S422 of FIG. 32 by the lighting device 420 or the device setting information after the change of the electrosurgical knife device 430 transmitted in S432 of FIG. 33 by the electrosurgical knife device 430.

After S407 of FIG. 30, as illustrated in FIG. 31, the tablet-type terminal device 440 reflects the change information transmitted in S407 of FIG. 30 by the video processor 410a in the trolley information stored in the storage unit 442, and updates the trolley information (S413 of FIG. 31).

Assume in this operation example that after S413 of FIG. 31, the video processor 410a has failed as illustrated in FIG. 30 (S408 of FIG. 30). In this case, information relating to the failure of the video processor 410a, the location of the alternative medical device thereof (the video processor 410b), or the like is reported to the user, for example, as described in the first embodiment.

After S408 of FIG. 30, as illustrated in FIG. 34, the user replaces the failed video processor 410a with the video processor 410b (S442 of FIG. 34).

After S442 of FIG. 34, as illustrated in FIG. 31, the tablet-type terminal device 440 reads out the device identification information from each of the RFID tag 412 of the video processor 410b, the RFID tag 421 of the lighting device 420, and the RFID tag 431 of the electrosurgical knife device 430 (see the lower side of FIG. 29), and compares it (actual trolley configuration information) with the trolley configuration information (the device identification information of each device of the video processor 410a, the lighting device 420, and the electrosurgical knife device 430) stored in the storage unit 442. As a result, due to the fact that the device identification information of the video processor 410 is different, the tablet-type terminal device 440 detects that the video processor 410 has been replaced (S414 of FIG. 31).

After S414 of FIG. 31, as illustrated in FIG. 35, the video processor 410b after the replacement performs a process of S451 to S453. Since this process is the same process as that of S402 to S404 of FIG. 30, their explanation is omitted here.

After S453 of FIG. 35, as illustrated in FIG. 32, the lighting device 420 performs a process of S423. Since this process is the same process as that of S421, its explanation is omitted here.

After S423 of FIG. 32, as illustrated in FIG. 35, the video processor 410b performs a process of S454. Since this process is the same process as that of S405 of FIG. 30, its explanation is omitted here.

After S454 of FIG. 35, as illustrated in FIG. 33, the electrosurgical knife device 430 performs a process of S433. Since this process is the same process as that of S431, its explanation is omitted here.

After S433 of FIG. 33, as illustrated in FIG. 35, the video processor 410b performs a process of S455. Since this process is the same process as that of S406 of FIG. 30, its explanation is omitted here.

After S455 of FIG. 35, as illustrated in FIG. 31, due to the fact that the video processor 410 has been replaced, the tablet-type terminal device 440 discards the device setting information of the video processor 410b from among the information transmitted in S455 of FIG. 35 by the video processor 410b. Further, the tablet-type terminal device 440 transmits to the video processor 410b the patient information, the inspection information, and the device setting information of the video processor 410 (i.e., the video processor 410a before the replacement) in the trolley information stored in the storage unit 442 (S415 of FIG. 31) (see the lower side of FIG. 29).

After S415 of FIG. 31, the video processor 410b reflects in the video processor 410b the patient information, the inspection information, and the device setting information of the video processor 410a transmitted in S415 of FIG. 31 by the tablet-type terminal device 440 (S456 of FIG. 35). That is, the video processor 410b stores the patient information and the inspection information of the video processor 410a in the storage unit 411 of the video processor 410b, and performs the device setting of the video processor 410b in accordance with the device setting information of the video processor 410a. Thereby, a state of the video processor 410b after the replacement is restored to that of the video processor 410a before the replacement.

After S456 of FIG. 35, as illustrated in FIG. 32, the lighting device 420 performs a process of S424. Since this process is the same process as that of S422, its explanation is omitted here.

After S424 of FIG. 32, as illustrated in FIG. 33, the electrosurgical knife device 430 performs a process of S434. Since this process is the same process as that of S432, its explanation is omitted here.

After S434 of FIG. 33, as illustrated in FIG. 35, the video processor 410b performs a process of S457. Since this process is the same process as that of S407 of FIG. 30, its explanation is omitted here.

After S457 of FIG. 35, as illustrated in FIG. 31, the tablet-type terminal device 440 performs a process of S416. Since this process is the same process as that of S413, its explanation is omitted here.

As described above, when S408 of FIG. 30, S416 of FIG. 31, S424 of FIG. 32, S434 of FIG. 33, S442 of FIG. 34, and S457 of FIG. 35 end, the operation example of the medical system 400 according to the present embodiment is completed.

As described above, according to the medical system 400 of the present embodiment, when the replacement of the video processor 410 is performed due to the failure or the like, the state (the patient information, the inspection information, and the device setting) of the video processor 410b after the replacement can be automatically restored to that of the video processor 410a before the replacement. Further, when the replacement of the peripheral device (the lighting device 420 or the electrosurgical knife device 430) is performed due to the failure or the like, the state (the device setting) of the peripheral device after the replacement can be automatically restored to that of the peripheral device before the replacement in the same way. Thereby, as in the conventional case, the user does not require a re-inputting of the patient information and the inspection information to the device (the video processor) after the replacement, or a resetting of the devices (the video processor, the lighting device, and the electrosurgical knife device) after the replacement, and a burden on the user caused by the device replacement can be reduced. Further, even if the device replacement is performed during the inspection, the inspection before the replacement and the inspection after the replacement can be treated as the same inspection, and therefore the inspection can be continued. Accordingly, as in the conventional case, the inspection is not interrupted for the device replacement during the inspection, and the inspection before the replacement and the inspection after the replacement are not treated as different inspections.

In the medical system 400 according to the present embodiment, various kinds of deformation are possible.

In the medical system 400 according to the present embodiment, for example, in addition to the trolley 450 on which the video processor 410, the lighting device 420, and the electrosurgical knife device 430 are mounted, a plurality of trolleys on which a plurality of the medical devices are mounted may be provided. In this case, for example, the tablet-type terminal device 440 may store the trolley information in the storage unit 442 for each trolley.

Further, in the medical system 400 according to the present embodiment, the tablet-type terminal device 340 may be equipped with the functions of the client terminal device 10 described in the first embodiment.

As described above, the first to the fourth embodiments are described. In each embodiment, for example, each device includes a hardware configuration of a CPU (Central Processing Unit), a ROM (Read Only Memory), a RAM (Random Access Memory), and the like, and a program stored in the ROM is stored in the RAM and executed by the CPU, and thereby, an operation of each device of the medical devices (the video processor, the scope, the lighting device, the electrosurgical knife device, etc.), the client terminal device, the tablet-type terminal device, and the server device is realized. Further, for example, the program may be stored in the RAM from external devices connected to the network (the network 70 etc.) and executed by the CPU. For example, each device may further include a hardware configuration of a medium reading device and the like, and the program may be stored in the RAM from a portable recording medium set in the medium reading device and executed by the CPU. In this case, as the portable recording medium, a variety of types of recording media, such as a CD-ROM (Compact Disc Read Only Memory), a flexible disk, an optical disk, a magnetic optical disk, a DVD (Digital Versatile Disc), and a USB memory can be used.

As described above, to facilitate understanding of the invention, the above-described embodiments show concrete examples of the invention, and the invention is not limited thereto. In the invention, various changes and modifications may be made without departing from the spirit of the invention and the scope of the appended claims.

As described above, according to the present invention, a server device, a medical system, and an information notification method can be provided in which when the device has failed, this fact can also be reported to a user that is not in the same room and the user can easily confirm the presence or absence, the location, or the like of the alternative device.

What is claimed is:

1. A medical system comprising:
  a server device;
  a first storage unit configured to store available device information including device names, locations, and scheduled use dates and times of a plurality of medical devices that are available for use;
  a processor configured to:
    determine whether one of the plurality of medical devices is a failed medical device;
    allow selection, from among the plurality of medical devices other than the failed medical device, an alternative medical device that may be an alternative device of the failed medical device on the basis of failure information of the failed medical device and the available device information stored in the first storage unit;
    transmit replacement information including a device name, a location, and a usable date and time of the alternative medical device to one or more client terminal devices corresponding to the medical devices that have not failed in order to display the replacement information on the one or more client terminal devices and instruct a user to select the alternative medical device for inspection; and
    automatically restore patient information and device setting information previously stored in the failed medical device,
  the plurality of medical devices including:
    an endoscopic device;
    a peripheral device connected to the endoscopic device, the failure information being transmitted from the endoscopic device that has detected a failure of the peripheral device; and
  a portable terminal device, wherein:
    the endoscopic device includes a second storage unit in which patient information and inspection information are stored,
    the endoscopic device transmits one or more of:
      the patient information stored in the second storage unit,
      the inspection information stored in the second storage unit,
      device setting information of the endoscopic device, and
      device setting information of the peripheral device acquired from the peripheral device to the portable terminal device,
    the portable terminal device includes:
      a third storage unit in which the patient information and the inspection information stored in the second storage unit, the device identification information and the device setting information of the endoscopic device, and the device identification information and the device setting information of the peripheral device are stored by being associated with each other;
      the processor further configured to:
        acquire one or both of device identification information of the endoscopic device and device identification information of the peripheral device;
        update corresponding information stored in the third storage unit in response to the patient information, the inspection information, the device setting information of the endoscopic device, or the device setting information of the peripheral device after a change transmitted by the endoscopic device; and
        compare the device identification information of the endoscopic device and the device identification information of the peripheral device acquired by the acquisition unit with the device identification information of the endoscopic device and the device identification information of the peripheral device stored in the third storage unit, wherein:
          as a result of the comparison, when the device identification information of the endoscopic device is different,
          the portable terminal device transmits the patient information, the inspection information, and the device setting information of the endoscopic device stored in the third storage unit to the endoscopic device,
          the endoscopic device stores the patient information and the inspection information transmitted by the portable terminal device in the second storage unit of the endoscopic device, and performs device setting of the endoscopic device in accordance with the device setting information of the endoscopic device transmitted by the portable terminal device, the comparison, when the device identification information of the peripheral device is different, the portable terminal device transmits the device setting information of the peripheral device stored in the third storage unit to the endoscopic device, and the endoscopic device performs device setting of the peripheral device in accordance with the device setting information of the peripheral device transmitted by the portable terminal device.

2. The medical system according to claim 1, wherein the processor is configured to transmit failed device information including a device name and a location of the failed medical device to all the client terminal devices, and transmits the replacement information including the device name, the location, and the usable date and time of the alternative medical device to the client terminal device close to the failed medical device.

3. The medical system according to claim 1, wherein the peripheral device includes one or more of scopes, lighting devices, and electrosurgical knife devices.

4. The medical system according to claim 1, wherein the failure information is one or more of:

patient information stored in a second storage unit of the endoscopic device, inspection information stored in the second storage unit, device identification information of the endoscopic device, device setting information of the endoscopic device, device identification information of the peripheral device that the endoscopic device acquires from the peripheral device, and device setting information of the peripheral device that the endoscopic device acquires from the peripheral device, the server device further includes:

a third storage unit in which the patient information and the inspection information stored in the second storage unit, the device identification information and the device setting information of the endoscopic device, and the device identification information and the device setting information of the peripheral device are stored by being associated with each other, wherein the processor is further configured to:

update corresponding information stored in the third storage unit in response to the patient information, the inspection information, the device setting information of the endoscopic device, or the device setting information of the peripheral device after a change transmitted by the endoscopic device; and compare the device identification information of the endoscopic device and the device identification information of the peripheral device transmitted by the endoscopic device with the device identification information of the endoscopic device and the device identification information of the peripheral device stored in the third storage unit, wherein:

as a result of the comparison, when the device identification information of the endoscopic device is different, the server device transmits the patient information, the inspection information, and the device setting information of the endoscopic device stored in the third storage unit to the endoscopic device, the endoscopic device stores the patient information and the inspection information transmitted by the server device in the second storage unit of the endoscopic device, and performs device setting of the endoscopic device in accordance with the device setting information of the endoscopic device transmitted by the server device, as a result of the comparison, when the device identification information of the peripheral device is different, the server device transmits the device setting information of the peripheral device stored in the third storage unit to the endoscopic device, and the endoscopic device performs device setting of the peripheral device in accordance with the device setting information of the peripheral device transmitted by the server device.

5. A medical system comprising:

the server device according to claim 1, and the plurality of medical devices including the endoscopic device and the peripheral device, wherein the endoscopic device includes:

a second storage unit in which patient information and inspection information are stored;

a third storage unit in which the patient information and the inspection information stored in the second storage unit, device identification information and device setting information of the endoscopic device, and device identification information and device setting information of the peripheral device acquired from the peripheral device are stored by being associated with each other, and that is freely attached to or detached from the endoscopic device, wherein the processor is further configured to:

update corresponding information stored in the third storage unit in response to a change in the patient information or the inspection information stored in the second storage unit, a change in device setting of the endoscopic device, or the device setting information after a change in the peripheral device acquired from the peripheral device; and compare the device identification information of the endoscopic device and the device identification information of the peripheral device acquired from the peripheral device with the device identification information of the endoscopic device and the device identification information of the peripheral device stored in the third storage unit, as a result of the comparison, when the device identification information of the endoscopic device is different, the endoscopic device stores the patient information and the inspection information stored in the third storage unit in the second storage unit of the endoscopic device, and performs device setting of the endoscopic device in accordance with the device setting information of the endoscopic device stored in the third storage unit, and as a result of the comparison, when the device identification information of the peripheral device is different, the endoscopic device performs device setting of the peripheral device in accordance with the device setting information of the peripheral device stored in the third storage unit.

6. An information notification method for a medical system including:

a plurality of medical devices;

one or more client terminal devices; and a server device including a storage unit that stores available device information including device names, locations, and scheduled use dates and times of the plurality of medical devices that are available for use, the server device being configured for:
  determining whether one of the plurality of medical devices is a failed medical device;
  allow selecting, from among the plurality of medical devices other than the failed medical device, an alternative medical device that maybe an alternative device of the medical device that has failed, on the basis of failure information including a device name and a location of the medical device that has failed and is at least one of the plurality of medical devices and the available device information stored in the storage unit;
  transmitting replacement information including a device name, a location, and a usable date and time of the alternative medical device to the one or more client terminal devices corresponding to the medical devices that have not failed in order to display the replacement information on the one or more client terminal devices and instruct a user to select the alternative medical device for inspection; and
  automatically restoring patient information and device setting information previously stored in the failed medical device;
the plurality of medical devices including:
  an endoscopic device;
  a peripheral device connected to the endoscopic device, the failure information being transmitted from the endoscopic device that has detected a failure of the peripheral device; and
a portable terminal device, wherein:
  the endoscopic device includes a second storage unit in which patient information and inspection information are stored,
  the endoscopic device transmits one or more of:
    the patient information stored in the second storage unit,
    the inspection information stored in the second storage unit,
    device setting information of the endoscopic device, and
    device setting information of the peripheral device acquired from the peripheral device to the portable terminal device,
  the portable terminal device includes:
    a third storage unit in which the patient information and the inspection information stored in the second storage unit, the device identification information and the device setting information of the endoscopic device, and the device identification information and the device setting information of the peripheral device are stored by being associated with each other;
  the processor further configured for:
    acquiring one or both of device identification information of the endoscopic device and device identification information of the peripheral device;
    updating corresponding information stored in the third storage unit in response to the patient information, the inspection information, the device setting information of the endoscopic device, or the device setting information of the peripheral device after a change transmitted by the endoscopic device; and
    comparing the device identification information of the endoscopic device and the device identification information of the peripheral device acquired by the acquisition unit with the device identification information of the endoscopic device and the device identification information of the peripheral device stored in the third storage unit, wherein:
    as a result of the comparison, when the device identification information of the endoscopic device is different,
    the portable terminal device transmits the patient information, the inspection information, and the device setting information of the endoscopic device stored in the third storage unit to the endoscopic device,
    the endoscopic device stores the patient information and the inspection information transmitted by the portable terminal device in the second storage unit of the endoscopic device, and performs device setting of the endoscopic device in accordance with the device setting information of the endoscopic device transmitted by the portable terminal device,
    the comparison, when the device identification information of the peripheral device is different, the portable terminal device transmits the device setting information of the peripheral device stored in the third storage unit to the endoscopic device, and
    the endoscopic device performs device setting of the peripheral device in accordance with the device setting information of the peripheral device transmitted by the portable terminal device.

* * * * *